(12) United States Patent
Lee et al.

(10) Patent No.: US 10,076,300 B2
(45) Date of Patent: Sep. 18, 2018

(54) RADIOGRAPHIC IMAGING APPARATUS AND A METHOD OF CONTROLLING THE SAME

(71) Applicant: SAMSUNG ELECTRONICS CO., LTD., Suwon-si (KR)

(72) Inventors: Hyeon Min Lee, Gunpo-si (KR); Geun Tae Bae, Anyang-si (KR); Qin Liu, Suwon-si (KR); Jeong Min Lee, Suwon-si (KR); WooYoung Jang, Seongnam-si (KR); Woo Sup Han, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 629 days.

(21) Appl. No.: 14/807,027

(22) Filed: Jul. 23, 2015

(65) Prior Publication Data

US 2016/0058406 A1 Mar. 3, 2016

(30) Foreign Application Priority Data

Aug. 27, 2014 (KR) .................. 10-2014-0112450

(51) Int. Cl.
*H05G 1/08* (2006.01)
*A61B 6/00* (2006.01)
*G16H 40/40* (2018.01)
(Continued)

(52) U.S. Cl.
CPC ............ *A61B 6/5211* (2013.01); *A61B 6/481* (2013.01); *A61B 6/487* (2013.01); *A61B 6/504* (2013.01);
(Continued)

(58) Field of Classification Search
CPC ....... A61B 6/5211; A61B 6/481; A61B 6/504; A61B 6/563; A61B 6/487; A61B 6/5258;
(Continued)

(56) References Cited

U.S. PATENT DOCUMENTS 6,701,341 B1 3/2004 Wu et al.
2002/0154824 A1 10/2002 Christensson et al.
(Continued)

FOREIGN PATENT DOCUMENTS

EP         1 381 314     10/2002
WO    WO 02083002 A1 * 10/2002 ............... H05G 1/26

OTHER PUBLICATIONS

International Search Report issued by International Searching Authority in corresponding International Application No. PCT/KR2015/007793, dated Oct. 28, 2015. (PCT/ISA/210).
(Continued)

*Primary Examiner* — Courtney Thomas
(74) *Attorney, Agent, or Firm* — Sughrue Mion, PLLC

(57) ABSTRACT

Disclosed herein are a radiographic imaging apparatus and a method of controlling the radiographic imaging apparatus. The radiographic imaging apparatus may include an imager configured to image a subject to obtain image data; a real-time processor configured to communicate with the imager and configured to obtain a real-time processing authority and perform real-time image processing on the image data; and a non-real-time processor configured to communicate with the imager and configured to perform non-real-time image processing on the image data, and in response to a failure occurring in the real-time processor, obtain the real-time processing authority and perform the real-time image processing on the image data.

28 Claims, 34 Drawing Sheets

(51) Int. Cl.
*G06T 1/20* (2006.01)
*G06F 19/00* (2018.01)
*G06F 11/20* (2006.01)

(52) U.S. Cl.
CPC ............ *A61B 6/5258* (2013.01); *G06F 19/00* (2013.01); *G06T 1/20* (2013.01); *G16H 40/40* (2018.01); *A61B 6/4225* (2013.01); *A61B 6/4233* (2013.01); *A61B 6/4291* (2013.01); *A61B 6/4441* (2013.01); *A61B 6/548* (2013.01); *A61B 6/563* (2013.01); *A61B 6/586* (2013.01); *A61B 2576/00* (2013.01); *G06F 11/202* (2013.01); *G06F 19/321* (2013.01)

(58) Field of Classification Search
CPC . A61B 6/4035; A61B 2576/00; A61B 6/4225; A61B 6/4233; A61B 6/4291; A61B 6/4441; G16H 40/40; G06F 19/3412; G06F 19/32
See application file for complete search history.

(56) References Cited

U.S. PATENT DOCUMENTS

| | | | |
|---|---|---|---|
| 2003/0026470 A1 | 2/2003 | Kasai | |
| 2003/0206609 A1* | 11/2003 | Kling | G06T 1/20 378/4 |
| 2010/0033586 A1 | 2/2010 | Kim | |
| 2011/0170667 A1* | 7/2011 | Ruggiero | A61B 6/461 378/98.5 |
| 2012/0210199 A1* | 8/2012 | Gale | G06F 11/1633 714/807 |
| 2013/0142309 A1 | 6/2013 | Iwakiri et al. | |

OTHER PUBLICATIONS

Communication dated Mar. 21, 2018 by the European Patent Office in counterpart European Patent Application No. 15835486.0.

* cited by examiner

RADIOGRAPHIC IMAGING APPARATUS AND A METHOD OF CONTROLLING THE SAME

CROSS-REFERENCE TO RELATED APPLICATION

This application claims priority from Korean Patent Application No. 10-2014-0112450, filed on Aug. 27, 2014 in the Korean Intellectual Property Office (KIPO), the entire contents of which are incorporated herein by reference.

BACKGROUND

1. Field

One or more exemplary embodiments relate to a radiographic imaging apparatus and a method of controlling the same.

2. Description of the Related Art

A radiographic imaging apparatus is an apparatus that applies radiation such as X-rays to a subject such as a human body or an object such as baggage and obtains and provides an image of an internal region of the object or the subject so that doctors or people can visually check tissues, structures, or objects inside the subject. Radiographic imaging apparatuses are widely utilized in various industrial fields such as the health industry, the security system industry, and the construction industry.

Radiographic imaging apparatuses can obtain and provide images of the internal region of subjects using properties that cause the radiation such as X-rays to be absorbed into a material or to be transmitted through the material depending on a property of the material within the subject, for example a density of the material. In general, the radiographic imaging apparatus can apply the radiation to the subject, receive the radiation that has passed through the subject, convert the radiation to an electrical signal, and use the electrical signal to produce a radiation image, thereby obtaining the radiation image representing the internal tissues and structures of the subject or the material within the object.

SUMMARY

Exemplary embodiments may provide a radiographic imaging apparatus capable of operating in real time without a stopping even when a failure occurs in the system, and a method of controlling the radiographic imaging apparatus.

In order to address the problems mentioned above, a radiographic imaging apparatus and a method of controlling the radiographic imaging apparatus are provided.

According to an exemplary embodiment, a radiographic imaging apparatus includes: an imaging unit configured to obtain image data from a subject; a real-time processing unit configured to communicate with the imaging unit and configured to obtain a real-time processing authority and perform real-time image processing on the image data; and a non-real-time processing unit configured to communicate with the imaging unit and configured to perform non-real-time image processing on the image data, wherein the non-real-time processing unit further configured to obtain the real-time processing authority and perform the real-time image processing on the image data, when a failure occurs in the real-time processing unit.

The real-time processing unit is further configured to transmit the real-time processing authority of the real-time processing unit to the non-real-time processing unit so that the non-real-time processing unit obtains the real-time processing authority, when a failure occurs in the real-time processing unit.

The non-real-time processing unit is further configured to activate the real-time processing authority of the imaging unit already stored in the non-real-time processing unit to obtain the real-time processing authority, when a failure occurs in the real-time processing unit.

The non-real-time processing unit is further configured to determine whether a failure occurs in the real-time processing unit on the basis of whether the non-real-time processing unit receives a signal transmitted from the real-time processing unit or content of the signal.

The real-time processing unit is further configured to notify the non-real-time processing unit of the occurrence of a failure when the failure occurs in the real-time processing unit.

The radiographic imaging apparatus may further include a central controller configured to control operations of the imaging unit, the real-time processing unit, and the non-real-time processing unit.

The central controller is further configured to sense whether a failure occurs in the real-time processing unit or the non-real-time processing unit.

The central controller is further configured to sense whether a failure occurs in the real-time processing unit or the non-real-time processing unit on the basis of a signal received from the real-time processing unit or the non-real-time processing unit.

The central controller transmits a confirmation signal to the real-time processing unit or the non-real-time processing unit, the real-time processing unit or the non-real-time processing unit transmits a response signal with respect to the confirmation signal to the central controller, and the central controller determines whether a failure occurs in the real-time processing unit or the non-real-time processing unit in accordance with the response signal.

The confirmation signal may include information on a sender and a receiver.

The real-time processing unit is further configured to generate the response signal to the confirmation signal and transmits the response signal to the central controller while processing the image in real time.

The central controller is further configured to control the non-real-time processing unit to obtain the real-time processing authority when a failure occurs in the real-time processing unit.

The central controller is further configured to control the real-time processing authority already stored in the central controller to be transmitted to the non-real-time processing unit so that the non-real-time processing unit obtains the real-time processing authority.

The central controller is further configured to transmit a control authority activation instruction to the non-real-time processing unit, and the non-real-time processing unit is further configured to activate the real-time processing authority already stored in the non-real-time processing unit to obtain the real-time processing authority in accordance with the control authority activation instruction.

The imaging unit, the real-time processing unit, the non-real-time processing unit, and the central controller may be configured to communicate with each other via a ring network.

The central controller is further configured to determine a control path in accordance with the occurrence of the failure, when a failure occurs in at least one of the imaging unit, the real-time processing unit, and the non-real-time processing unit.

The central controller is further configured to transmit a control signal to the non-real-time processing unit via the real-time processing unit, when no failure occurs in the real-time processing unit.

The central controller is further configured to transmit a control signal to the non-real-time processing unit along a path that does not include the real-time processing unit, when a failure occurs in the real-time processing unit.

The real-time processing unit, and the non-real-time processing unit, the central controller records the occurrence of the failure, when a failure occurs in any one of the imaging unit.

The imaging unit, the real-time processing unit, and the non-real-time processing unit may be configured to communicate with each other via a ring network.

The imaging unit may comprise an adaptor configured to connect an operating unit having a non-standard interface to a network transmitting data in accordance with a predefined standard.

The operating unit comprises at least one of a radiation applying unit configured to generate radiation to be applied to the subject and apply the radiation in the subject direction, a collimator configured to filter the radiation generated in the radiation unit, an anti-scatter grid configured to filter the radiation that has passed through the subject, and a radiation detecting unit configured to receive the radiation that has passed through the subject and obtain the image data.

At least two of the imaging unit, the real-time processing unit, and the non-real-time processing unit may be directly connected by individually provided communication ports.

The real-time processing unit is further configured to transmit one or more real-time images and associated data obtained by the real-time image processing to the non-real-time processing unit while performing the real-time image processing.

The associated data may include detailed information on the real-time image or a history associated with the real-time image processing.

The non-real-time processing unit executes the same application as the application for the real-time control of the real-time processing unit, when the non-real-time processing unit obtains a control authority regarding real-time control of the imaging unit.

The non-real-time image processing may include generation of a three-dimensional radiation image.

The non-real-time image processing may include at least one of generation of a real-time radiation image and digital subtraction angiography (DSA) processing.

According to an aspect of another exemplary embodiment, a medical imaging apparatus is provided, which includes: an imaging unit configured to image a subject to obtain image data, a real-time processing unit configured to control a real-time operation of the imaging unit in accordance with a control authority regarding real-time control of the imaging unit and a non-real-time processing unit configured to perform non-real-time processing of the imaging unit, wherein the non-real-time processing unit obtains the control authority regarding real-time control of the imaging unit and control the real-time operation of the imaging unit in accordance with the control authority, when a failure occurs in the real-time processing unit.

The medical imaging apparatus may further include a central controller configured to control operations of the imaging unit, the real-time processing unit, and the non-real-time processing unit, and sense whether a failure occurs in the real-time processing unit.

According to an aspect of another exemplary embodiment, a method of controlling a radiographic imaging apparatus including an image unit configured to image a subject to obtain image data, a real-time processing unit configured to perform real-time image processing on the image data, and a non-real-time processing unit configured to perform non-real-time image processing on the image data is provided, and the method includes: obtaining, by the imaging unit, the image data; performing, by the real-time processing unit, the real-time image processing on the image data in accordance with a real-time processing authority; obtaining, by the non-real-time processing unit, the real-time processing authority of the image data when a failure occurs in the real-time processing unit; and performing, by the non-real-time processing unit, the real-time image processing on the image data.

The method may further include transmitting, by the real-time processing unit, the real-time processing authority of the real-time processing unit to the non-real-time processing unit when a failure occurs in the real-time processing unit.

Obtaining, by the non-real-time processing unit, the real-time processing authority of the image data when a failure occurs in the real-time processing unit may include activating, by the non-real-time processing unit, the real-time processing authority of the imaging unit already stored in the non-real-time processing unit to obtain the real-time processing authority when the failure occurs in the real-time processing unit.

Obtaining, by the non-real-time processing unit, the real-time processing authority of the image data when a failure occurs in the real-time processing unit may further include determining whether a failure occurs in the real-time processing unit on the basis of whether a signal transmitted from the real-time processing unit or content of the signal is received.

The radiographic imaging apparatus may further include a central controller configured to control operations of the imaging unit, the real-time processing unit, and the non-real-time processing unit.

The method may further include sensing, by the central controller, the occurrence of a failure of the real-time processing unit or the non-real-time processing unit.

Sensing, by the central controller, the occurrence of a failure of the real-time processing unit may include: transmitting, by the central controller, a confirmation signal to the real-time processing unit or the non-real-time processing unit; transmitting, by the real-time processing unit or the non-real-time processing unit, a response signal with respect to the confirmation signal to the central controller; and sensing, by the central controller, whether a failure occurs in the real-time processing unit or the non-real-time processing unit in accordance with the response signal.

The method may further include controlling, by the central controller, the non-real-time processing unit to obtain the real-time processing authority when a failure occurs in the real-time processing unit.

Controlling, by the central controller, the non-real-time processing unit to obtain the real-time processing authority when a failure occurs in the real-time processing unit may include controlling, by the central controller, the real-time processing authority already stored in the central controller to be transmitted to the non-real-time processing unit to cause the non-real-time processing unit to obtain the non-real-time processing unit.

Controlling, by the central controller, the non-real-time processing unit to obtain the real-time processing authority when a failure occurs in the real-time processing unit may include transmitting a control authority activation instruction to the non-real-time processing unit and causing the non-real-time processing unit to activate the real-time processing authority already stored in the non-real-time processing unit in accordance with the control authority activation instruction.

The imaging unit, the real-time processing unit, the non-real-time processing unit, and the central controller may be configured to communicate with each other via a ring network.

The central controller may sequentially transmit a control signal to any one of the imaging unit, the real-time processing unit, and the non-real-time processing unit in the sequence in which they are connected.

The central controller may change a control path in accordance with the occurrence of a failure when the failure occurs in at least one of the imaging unit, the real-time processing unit, and the non-real-time processing unit.

The method may further include recording that a failure occurs when the failure occurs in any one of the real-time processing unit and the non-real-time processing unit.

The imaging unit may include an operating unit having a non-standard interface, and an adaptor connecting the operating unit having the non-standard interface to a network transmitting data in accordance with a predefined standard.

The method may further include transmitting, by the real-time processing unit, a real-time image and associated data to the non-real-time processing unit while the real-time processing unit performs the real-time image processing.

According to the radiographic imaging apparatus and the method of controlling the radiographic imaging apparatus as described above, the radiographic imaging apparatus can operate in real time without stopping even when a failure occurs in the system.

According to the radiographic imaging apparatus and the method of controlling the radiographic imaging apparatus as described above, the radiographic imaging apparatus can be restored in real time even when a failure occurs in the system.

According to the radiographic imaging apparatus and the method of controlling the radiographic imaging apparatus as described above, it is possible to prevent a system from stopping due to a failure occurring in the system, and thus it is not necessary to reboot the system due to system stoppage. It is possible to prevent a subject such as an examinee from having to wait a long time for the reboot and to solve problems that various phenomena occurring within the subject are not imaged during the reboot.

According to the radiographic imaging apparatus and the method of controlling the radiographic imaging apparatus as described above, it is also possible to have an effect of preventing a diagnosis, procedure, or operation from being stopped or failing due to system stoppage caused by a failure.

According to the radiographic imaging apparatus and the method of controlling the radiographic imaging apparatus as described above, it is possible to prevent over-radiation or mis-radiation from being unintentionally applied to the subject due to system stoppage caused by a failure. In addition, it is possible to prevent a radiation exposure accident by blocking the radiation from being applied to an unintended position.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION OF EXEMPLARY EMBODIMENTS

Figure 1:
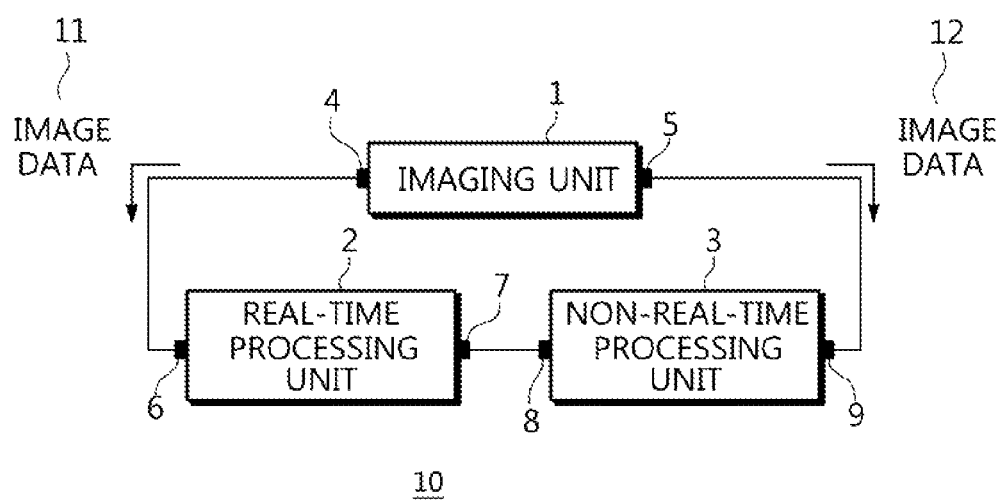
FIG. 1 is a conceptual view illustrating an exemplary embodiment of a radiographic imaging apparatus.

Reference will now be made in detail to exemplary embodiments, which are illustrated in the accompanying drawings, wherein like reference numerals refer to like elements throughout.

Hereinafter, an exemplary embodiment of the radiographic imaging apparatus will be described with reference to FIG. 1. FIG. 1 is a conceptual view illustrating an exemplary embodiment of a radiographic imaging apparatus.

Referring to FIG. 1, the radiographic imaging apparatus 10 may include an imaging unit 1 (e.g. an imager, etc.) that obtains image data, a real-time processing unit 2 (e.g., a real-time processor, etc.) that performs real-time image processing on the image data, and a non-real-time processing unit 3 (e.g., a non-real-time processor, etc.) that performs non-real-time image processing on the image data.

The real-time processing unit 2 may process the image data within a real-time constraint or deadline, e.g., a predetermined time. The non-real-time processing unit 3 may process the image data without being subject to the same real-time constraint or deadline. However, according to an exemplary embodiment, when real-time processing authority is obtained by the non-real-time processing unit 3, the non-real-time processing unit 3 may process the image data subject to the real-time constraint or deadline.

The imaging unit 1 may obtain the image data using visible rays, ultrasonic waves, or radiation. The imaging unit 1 may obtain the image data by obtaining an electrical signal induced by magnetic resonance resulting from an applied magnetic field. In this case, the obtained image data may be raw data. Various apparatuses may be used to implement the imaging unit 1. For example, a general camera, an ultrasonic probe, a digital radiography (DR) imaging apparatus, a computed tomography (CT) apparatus, a mammography apparatus, a fluoroscopy apparatus, a magnetic resonance imaging (MRI) apparatus, a single photon emission computed tomography (SPECT) apparatus, and so forth may be used to implement the imaging unit 1. In addition, any of various apparatuses that may be considered by those skilled in the art may be examples of the imaging unit 1.

The real-time processing unit 2 may be configured to communicate with the imaging unit 1. According to an exemplary embodiment, the real-time processing unit 2 may receive image data transmitted from the imaging unit 1 and perform real-time image processing on the received image data. According to another exemplary embodiment, the real-time processing unit 2 may control a real-time operation of the imaging unit 1. According to yet another exemplary embodiment, the real-time processing unit 2 may perform both of the real-time image processing and the real-time operation control of the imaging unit 1.

The real-time processing unit 2 may operate in accordance with a real-time processing authority. According to an exemplary embodiment, the real-time processing authority may include a processing authority associated with the real-time image processing of the image data. Real-time processing authority may include the authority receive image data, control communication with an imagining unit, and control the processing of the image data. According to another exemplary embodiment, the real-time processing authority may include an authority for controlling a real-time operation of the imaging unit 1. An application for performing the real-time processing may be installed in the real-time processing unit 2. When the real-time processing unit 2 obtains the real-time processing authority, the application may be executed in accordance with the real-time processing authority. For example, when the real-time processing unit 2 obtains the real-time processing authority, the real-time processing unit may load the application for performing the real-time processing onto a system or perform the real-time image processing on the image data input from the loaded application. In this case, the application may be a set of a series of computer programs. When the application is loaded onto the system, the system may execute specific operations in accordance with the application.

The real-time image processing may include a procedure for generating and processing the real-time image. The real-time image processing may not require many resources at the time of processing the image, or may include various types of image processing through which data can be processed quickly for various reasons including a small amount of data to be processed. When the imaging unit 1 is a fluoroscopy apparatus, the real-time image processing may include real-time generation of the radiation image, real-time correction of the radiation image, or digital subtraction angiography (DSA) processing. In DSA processing, an image before contrast medium injection and an image after contrast medium injection are obtained and the two images are subjected to the subtraction processing to extract only contrasted blood vessels.

According to an exemplary embodiment, the real-time processing unit 2 may perform the real-time control on the imaging unit 1. In particular, the real-time processing unit 2 may control real-time operations of the imaging unit 1 such as a movement of the radiation applying unit or irradiation.

The non-real-time processing unit 3 may be configured to communicate with the image unit 1, receive image data transmitted from the image unit 1, and perform non-real-time image processing on the received image data. An application for the non-real-time image processing may be installed in the non-real-time processing unit 3. The non-real-time processing unit 3 may also run the application in accordance with the non-real-time image processing authority for the non-real-time processing or perform the non-real-time image processing using the application. In some exemplary embodiments, no authority may be set to be requested for the non-real-time imaging processing of the non-real-time processing unit 3.

The non-real-time image processing may include a procedure for generating and processing the non-real-time image. The non-real-time image processing may require many resources for processing the image, or may include various types of image processing for image data that is difficult to process rapidly for various reasons including a large amount of data to be processed. For example, when the imaging unit 1 is a fluoroscopy apparatus, the non-real-time image processing may include generation of the non-real-time radiation image, non-real-time correction of the stereoscopic radiation image, generation of a three-dimensional stereoscopic image, the volume data processing, or the like.

According to an exemplary embodiment, when it is difficult for the real-time processing unit 2 to perform the real-time image processing because of a failure or fault occurring in the real-time processing unit 2, the non-real-time processing unit 3 may obtain a real-time processing authority and then perform the real-time image processing in accordance with the obtained real-time processing authority. As an example, when a failure occurs in the real-time processing unit 2, the non-real-time processing unit 3 may activate the real-time processing authority already stored in a storage device of the non-real-time processing unit 3 to obtain the real-time processing authority, and then perform the real-time image processing on the image data imaged by the imaging unit 1. As another example, when a failure occurs in the real-time processing unit 2, the non-real-time processing unit 3 may receive the real-time processing authority from the real-time processing unit 2 and then perform the real-time image processing in accordance with the received real-time processing authority.

The non-real-time processing unit 3 may determine whether a failure occurs in the real-time processing unit 2 using various methods. For example, the non-real-time processing unit 3 may determine whether a failure occurs in the real-time processing unit 2 on the basis of a failure occurrence signal transmitted from the real-time processing unit 2, and may determine whether a failure occurs in the real-time processing unit 2 on the basis of whether the non-real-time processing unit receives a response signal from the real-time processing unit 2 which corresponds to the signal transmitted from the non-real-time processing unit 3.

According to an exemplary embodiment, the non-real-time processing unit 3 may perform the non-real-time control on the imaging unit 1. In addition, the non-real-time processing unit 3 may run various applications for user convenience in addition to the non-real-time processing application. For example, the non-real-time processing unit 3 may run a clinical application program such as a patient management program to provide information on the patient or receive and store information on the patient's status.

The imaging unit 1, the real-time processing unit 2, and the non-real-time processing unit 3 may be configured to communicate with each other via a ring network. In particular, the imaging unit 1 and the real-time processing unit 2 may be connected to each other, the real-time processing unit 2 and the non-real-time processing unit 3 may be connected to each other, and the imaging unit 1 and the non-real-time processing unit 3 may be connected to each other, thereby forming a ring network. Various data such as image data obtained by the imaging unit 1 may be transmitted in at least one of directions 11 and 12. In other words, the imaging unit 1 may transmit image data 11 to the real-time processing unit 2 and transmit image data 12 to the non-real-time processing unit 3. In addition, data transmitted from the imaging unit 1 may be transmitted directly or indirectly to the real-time processing unit 2 or the non-real-time processing unit 3. In other words, the imaging unit 1 may directly transmit image data to the real-time processing unit 2 and indirectly transmit image data to the real-time processing unit 2 via the non-real-time processing unit 3.

According to an exemplary embodiment, data transmission directions 11 and 12 may be determined in accordance with a status of the real-time processing unit 2 or the non-real-time processing unit 3. For example, when no failure occurs in the real-time processing unit 2, image data of the imaging unit 1 may be directly transmitted to the non-real-time processing unit 3 or indirectly transmitted to the non-real-time processing unit via the real-time processing unit 2. However, when a failure occurs in the real-time processing unit 2, image data of the imaging unit 1 may be set to be only directly transmitted to the non-real-time processing unit 3.

According to exemplary embodiments, the imaging unit 1, the real-time processing unit 2, and the non-real-time processing unit 3 may be provided with respective communication modules 4 to 9 for communicating with the outside. The communication modules 4 to 9 may transmit or receive data using a wired network or a wireless network. According to an exemplary embodiment, the communication modules 4 to 9 may include communication ports to be coupled with cables. According to another exemplary embodiment, the communication modules 4 to 9 may include antennas for radiating or receiving electromagnetic waves with predetermined frequencies, modems that modulate or demodulate signals, and so forth. All of the communication modules 4 to 9 may transmit and receive data in the same manner, and some of the communication modules 4 to 9 may transmit and receive data in a different manner from the other communication modules.

Figure 2:
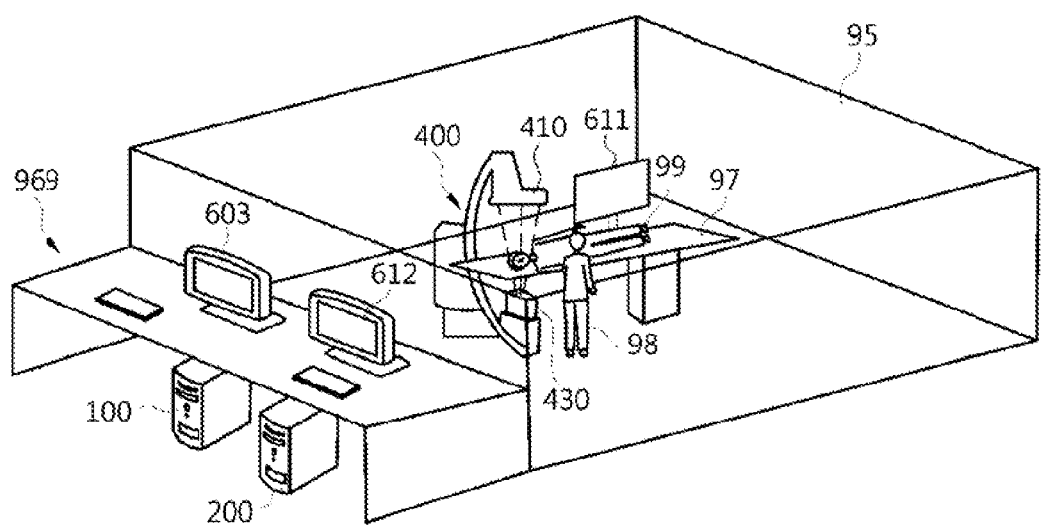
FIG. 2 is a view illustrating an exemplary embodiment of an imaging room in which a radiographic imaging apparatus is implemented.

Hereinafter, various exemplary embodiments of the radiographic imaging apparatus will be described in more detail with reference to FIGS. 2 to 25. FIG. 2 is a view illustrating an exemplary embodiment of an imaging room in which the radiographic imaging apparatus is implemented, and FIG. 3 is a configuration view illustrating an exemplary embodiment of the radiographic imaging apparatus.

As shown in FIG. 2, the radiographic imaging apparatus 10 may be installed in the imaging room 95 for imaging the subject 99, each part of the radiographic imaging apparatus 10 may be installed in a predetermined position within the imaging room 95. Referring to FIGS. 2 and 3, the radiographic imaging apparatus 10 may include a real-time processing unit 100, a non-real-time processing unit 200, a central controller 300, a radiation imaging unit 400 (e.g., a radiation imager, etc.), a switcher 600, and a display 610. According to an exemplary embodiment, the real-time processing unit 100, the non-real-time processing unit 200, the central controller 300, the radiation imaging unit 400, the switcher 600, and the display 610 may all be installed within the imaging room 95. According to another exemplary embodiment, some parts of the radiographic imaging apparatus 10 may be installed within the imaging room 95 and others may be installed in a different space 95a outside the imaging room 95. For example, the real-time processing unit 100, the non-real-time processing unit 200, the switcher 600, and one of the displays 610, that is, a second display 612, may be installed in the space 95a outside the imaging room 95. The radiation imaging unit 400 may be installed within the imaging room 95. A stand 97 on which the subject 99 to be imaged by the radiation imaging unit 400 may be held may be installed within the imaging room 95. A first display 611 for providing a user, for example, an operator 98, with a real-time image may be further installed within the imaging room 95. In the meantime, a console 603 for controlling the radiographic imaging apparatus 10 may be provided inside the imaging room 95 or in the space 95a outside the imaging room, and the user 98 may manipulate or use the console 603 to control operations of the radiographic imaging apparatus 10.

Figure 3:
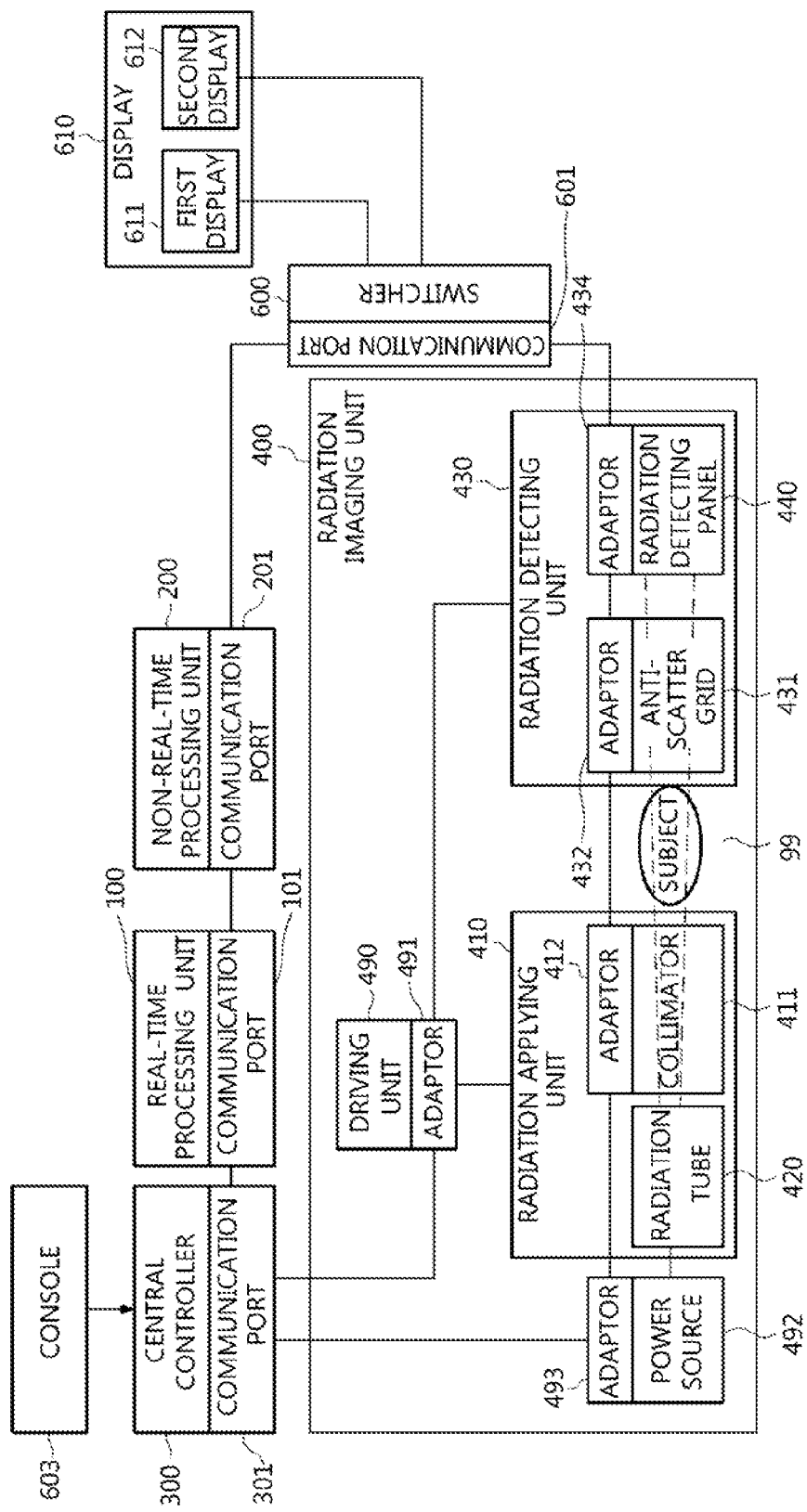
FIG. 3 is a configuration view illustrating an exemplary embodiment of a radiographic imaging apparatus.

Referring to FIG. 3, the real-time processing unit 100, the non-real-time processing unit 200, the central controller 300, the radiation imaging unit 400, and the switcher 600 of the radiographic imaging apparatus 10 may be communicatively connected via a network. Image data generated by the radiation imaging unit 400, and various signals output from the real-time processing unit 100, the non-real-time processing unit 200, or the central controller 300 may be transmitted to another apparatus 100 to 400 or 600 via the network. The real-time processing unit 100, the non-real-time processing unit 200, the central controller 300, the radiation imaging unit 400, and the switcher 600 may be communicatively connected via the ring network. In other words, as shown in FIG. 3, components of the radiographic imaging apparatus 10 may be serially connected in the order of the real-time processing unit 100, the central controller 300, the radiation imaging unit 400, the switcher 600, and the non-real-time processing unit 200. In addition, the non-real-time processing unit 200 may be directly connected serially to the real-time processing unit 100. This arrangement order may be arbitrarily changed by selection of a system designer. For example, components of the radiographic imaging apparatus 10 may be arranged in the order of the real-time processing unit 100, the non-real-time processing unit 200, the central controller 300, the radiation imaging unit 400, and the switcher 600. When the components of the radiographic imaging apparatus 10 are connected via the ring network, control signals or data may be transmitted clockwise or counterclockwise on the basis of FIG. 3. In addition, the control signals or the data may be transmitted in a full-duplex manner at the same time or at different times. In other words, the control signals or the data may be transmitted at the same or at different times either clockwise or counterclockwise. For example, the control signal output from the central controller 300 may be transmitted to the real-time processing unit 100, transmitted to the radiation imaging unit 400, and transmitted to both of the real-time processing unit 100 and the radiation imaging unit 400 at the same time or at different times. The signal transmitted to the real-time processing unit 100 may be transmitted in the order of the non-real-time processing unit 200, the switcher 600, and the radiation imaging unit 400. The signal transmitted to the radiation imaging unit 400 may be transmitted in the order of the non-real-time processing unit 200 and the real-time processing unit 100. Accordingly, the real-time processing unit 100, the non-real-time processing unit 200, the central controller 300, the radiation imaging unit 400, and the switcher 600, and the ring network may be implemented as a bidirectional serial field bus.

According to an exemplary embodiment, the real-time processing unit 100, the non-real-time processing unit 200, the central controller 300, the radiation imaging unit 400, and the switcher 600 may include communication ports 101, 201, 301, and 601 and adaptors 412, 432, 434, 491, and 493 so that they can communicate with each other.

The communication ports 101, 201, 301, and 601 may provide a function of connecting the apparatus with a cable through which data can be transmitted or received. The communication ports 101, 201, 301, and 601 may include all of serial ports and parallel ports. For example, the communication ports 101, 201, 301, and 601 may be communication ports into which terminals of a UTP cable are inserted, and may be Universal Serial Bus (USB) ports into which USB terminals are inserted. In addition, various means that can be used for the communication may be examples of the communication ports 101, 201, 301, and 601.

The communication ports 101, 201, 301, and 601 may be installed in at least one of the real-time processing unit 100, the non-real-time processing unit 200, the central controller 300, and respective operating units 411, 431, 440, 490 and 493 (e.g., operating devices, etc.) of the radiation imaging unit 400 (e.g., a radiation imager, etc.), and the switcher 600. In some exemplary embodiments, the communication ports 101, 201, 301, and 601 may be installed in only some of the real-time processing unit 100, the non-real-time processing unit 200, the central controller 300, and respective operating units 411, 431, 440, 490 and 493 of the radiation imaging unit 400, and the switcher 600.

According to other exemplary embodiments, antennas and wireless communication chips that can wirelessly transmit and receive data instead of the communication ports 101, 201, 301, and 601 may be provided in the real-time processing unit 100, the non-real-time processing unit 200, the central controller 300, the radiation imaging unit 400, and the switcher 600. For example, the wireless communication chip may be a communication chip for performing wireless communication using at least one of Bluetooth, near field communication (NFC), Zigbee, Wireless-Fidelity (WiFi), WiFi Direct, Infrared Data Association (IrDA), Home RF, and Ultra Wide Band (UBW).

According to an exemplary embodiment, as shown in FIG. 3, the adaptors 412, 432, 434, 491, and 493 may be provided in respective operating units 411, 431, 440, 490, and 493 of the radiation imaging unit 400 instead of the communication ports 101, 201, 301, and 601. The adaptors 412, 432, 434, 491, and 493 may implement an interface between the network of the radiographic imaging apparatus 10 and the respective operating units 411, 431, 440, 490, and 493 of the radiation imaging unit 400. For example, the respective operating units 411, 431, 440, 490, and 492 of the radiation imaging unit 400 may interface with an outside in a non-standard manner such as serial communication with low speed and low band while data is transmitted in the network in accordance with a predefined standard. In this case, the adaptors 412, 432, 434, 491, and 493 may connect the operating unit having the non-standard interface to the network transmitting data in accordance with the predefined standard. According to the adaptors 412, 432, 434, 491, and 493 as described above, it is possible to prevent the performance of the real-time operation from being degraded and the complexity of the system from being increased due to limitations of the operating units 411, 431, 440, 490, and 493. The adaptors 412, 432, 434, 491, and 493 may implement profiles of the respective operating units 411, 431, 440, 490, and 492 operating in a typical manner using the real-time fieldbus slave stack, and transmit data in real time or perform associated control.

The radiation imaging unit 400 may obtain image data with respect to the subject 99 as shown in FIGS. 2 and 3. In particular, the radiation imaging unit 400 may obtain the radiation image with respect to the subject 99 using the radiation. The radiation imaging unit 400 may be a DR imaging apparatus, a CT apparatus, a mammography apparatus, a fluoroscopy apparatus, or a SPECT apparatus.

Hereinafter, the DR imaging apparatus will be described as an example of the radiation imaging unit 400 with reference to FIGS. 3 to 7.

Figure 4:
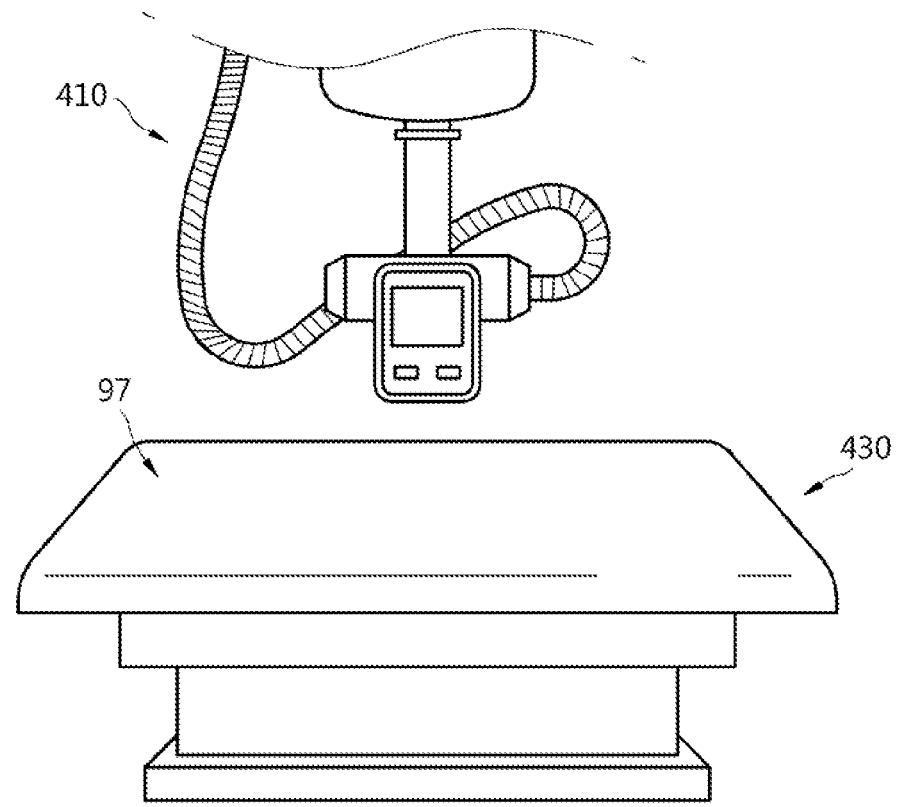
FIG. 4 is a view illustrating an exemplary embodiment of a digital radiography (DR) imaging apparatus.
Figure 5:
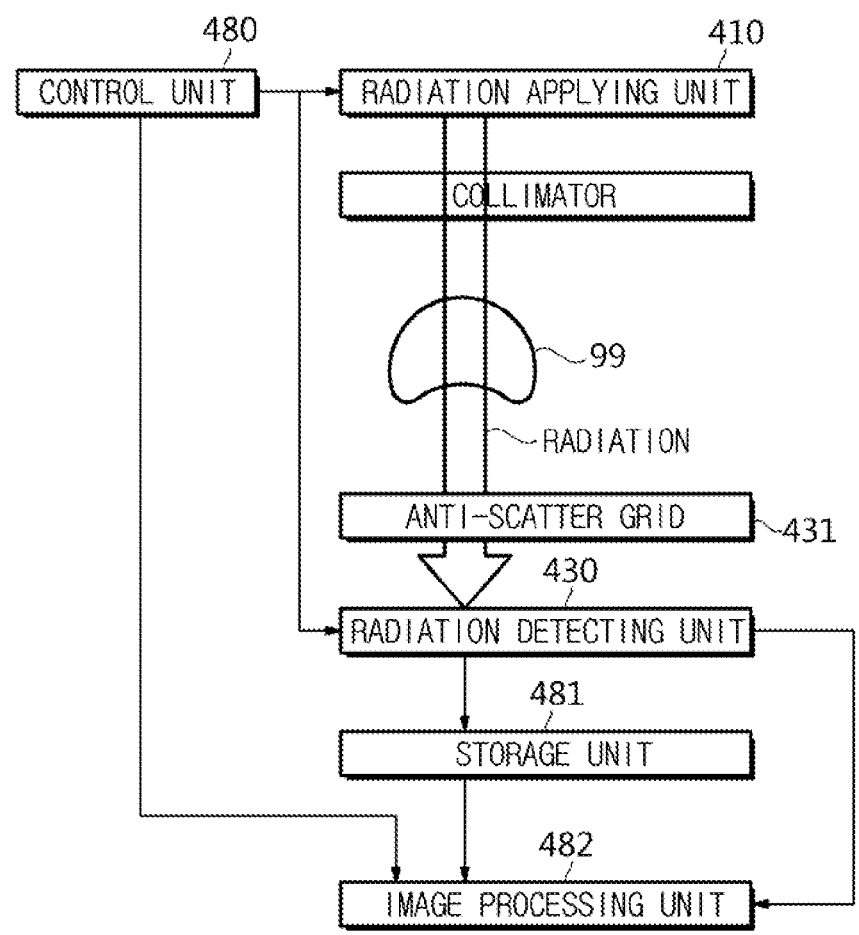
FIG. 5 is a block diagram illustrating an exemplary embodiment of a DR imaging apparatus.

FIG. 4 is a view illustrating an exemplary embodiment of the DR imaging apparatus, and FIG. 5 is a block diagram illustrating an exemplary embodiment of the DR imaging apparatus. As shown in FIG. 4, the DR imaging apparatus may include a radiation applying unit 410 (e.g., a radiation applier, etc.) applying radiation to the subject 99 and a radiation detecting unit 430 (e.g., a radiation detector, etc.) detecting the radiation that has passed through the subject 99. The radiation applying unit 410 may be designed so that it is movable and so that its position may be adjusted. The radiation detecting unit 430 may be disposed in a position at which the radiation that has passed through the subject 99 can be received, and may be provided within the stand 97 on which the subject 99 may be held if necessary. As shown in FIG. 5, the DR imaging apparatus may include a radiation applying unit 410, a radiation detecting unit 430, an input unit 479 (e.g., an input device, etc.), a control unit 480 (e.g., a controller, etc.), a storage unit 481 (e.g., a storage, memory, etc.), an image processing unit 482 (e.g., an image processor, etc.), and a display 483.

The radiation applying unit 410 may generate the radiation according to the tube voltage and the tube current to apply the radiation to the subject 99. Referring to FIG. 3, the radiation applying unit 410 may include a radiation tube 420 generating and applying the radiation, and a collimator 411 filtering the radiation generated in the radiation tube 420. In some exemplary embodiments, the radiation applying unit 410 may include a plurality of radiation tubes 420.

Figure 6:
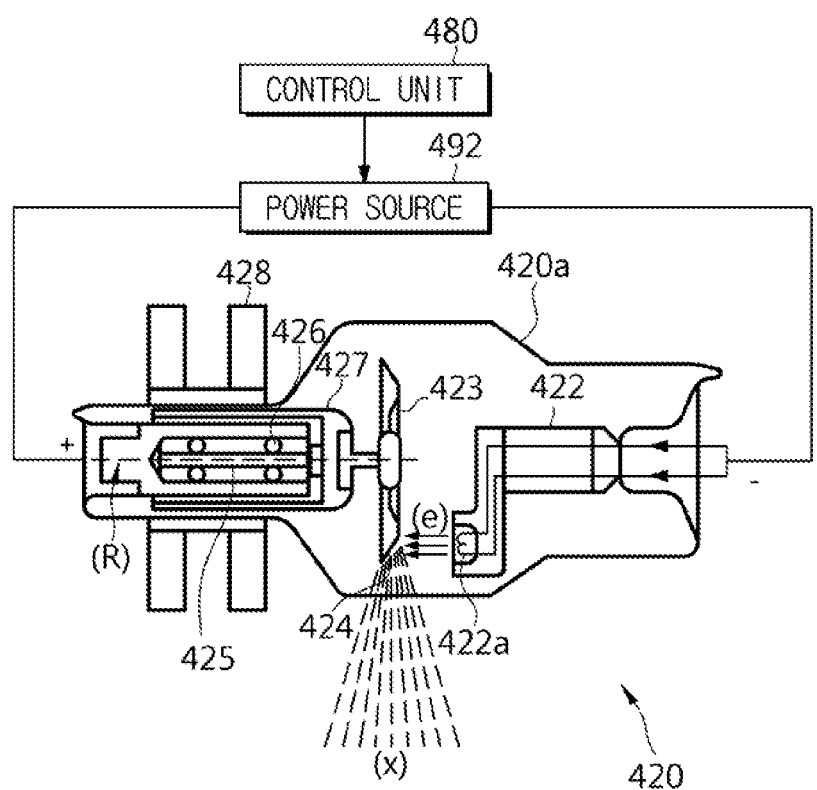
FIG. 6 is a view illustrating an exemplary embodiment of a radiation applying unit.

FIG. 6 is a view illustrating an exemplary embodiment of the radiation tube. Referring to FIG. 6, the radiation tube 420 may be electrically connected to a power source 492.

The power source 492 may apply a predetermined voltage and a predetermined current to the radiation tube 420 under the control of the control unit 480. The power source 492 may be a commercial power source or a separate electric generator. In addition, the power source 492 may be a storage battery provided within the radiation imaging unit 400.

When the predetermined voltage and current are applied to the radiation tube 420 from the power source 492, the radiation tube 420 may generate the radiation with a constant magnitude in accordance with the applied predetermined voltage and current. The radiation tube 420 may include a tubular body 420*a*, a cathode 422, and an anode 423. The tubular body 420*a* may have various components necessary to generate the radiation such as the cathode 422 and the anode 423 fixed stably therein and may shield electrons (e) from leaking out. The tubular body 420*a* may be a glass tube formed of a predetermined silicate hard glass. The degree of vacuum within the tubular body 420*a* may be kept at a high level of about 10-7 mmHg. Electron beams (e) may be radiated from the cathode 422 toward the anode 423. A filament 422*a* on which electrons are concentrated may be provided at the end of the cathode 422. The filament 422*a* is heated by the applied tube voltage to cause the concentrated electrons to be emitted into the tubular body 420*a*, and the emitted electrons (e) are accelerated within the tubular body 420*a* to move toward the anode 423. The filament 422*a* of the cathode 422 may be formed of a metal such as tungsten (W). In some exemplary embodiments, carbon nanotubes may be provided in the cathode 422 instead of the filament 422*a*. The radiation may be generated in the anode 423. When the moving electrons (e) collide with the target surface 424 of the anode 423, the radiation x having an energy corresponding to the tube voltage is generated in the target surface 424 in accordance with the rapid decrease in electrons (e). The target surface 424 is cut in a constant direction as shown in FIG. 6, so that the radiation x may be mainly applied in the predetermined direction. The anode 423 may be formed a metal such as copper (Cu), and the target surface 424 may be formed of a metal such as W, chromium (Cr), iron (Fe), or nickel (Ni). The anode 423 may be a rotational anode having a circular plate shape as shown in FIG. 6. The end portion of the rotational anode 423 may be cut at a predetermined angle and the target surface 424 may be formed in the cut surface. The rotational anode 423 may rotate at a predetermined speed about a predetermined axis R. In order to allow the rotational anode 423 to rotate, the radiation tube 420 may be provided with a stator generating a rotational magnetic field, a rotor 427 rotating according to the rotational magnetic field generated in the stator 428 to cause the rotational anode 423 to rotate, a bearing 426 rotating according to rotation of the rotor, and an axis member 425 acting as the rotational axis R of the rotational anode 423. The rotor 427 may be a permanent magnet. According to an exemplary embodiment, the anode 423 may be a fixed anode having a cylindrical shape with a cut surface cut at a predetermined cutting angle, and the target surface 424 may be formed in the cut surface.

The control unit 480 may be implemented by one or more semiconductor chips, a printed circuit board in which the semiconductor chips are provided, and so forth. The control unit 480 may be implemented by a control apparatus such as a processor provided within the DR imaging apparatus, and may be implemented by the central controller 300. In addition, the control unit 480 may be implemented by the real-time processing unit 100 or the non-real-time processing unit 200.

The collimator 411 guides radiation to the constant region in a specific direction by filtering radiation radiated from the radiation tube 420. The collimator 411 may include openings through which the radiation applied in a specific direction passes and collimator blades that absorb the radiation applied in other directions. The user may control the direction and range of application of the radiation using the size or position of the openings of the collimator 411. The collimator blades of the collimator 411 may be formed of a material that can absorb the radiation such as lead (Pb).

As shown in FIGS. 3 and 5, the radiation x applied from the radiation applying unit 410 is applied to the subject 99 held on the stand 97, and the radiation that has passed through the subject 99 may pass through an anti-scatter grid 431 and then reach a radiation detecting panel 440.

Figure 7:
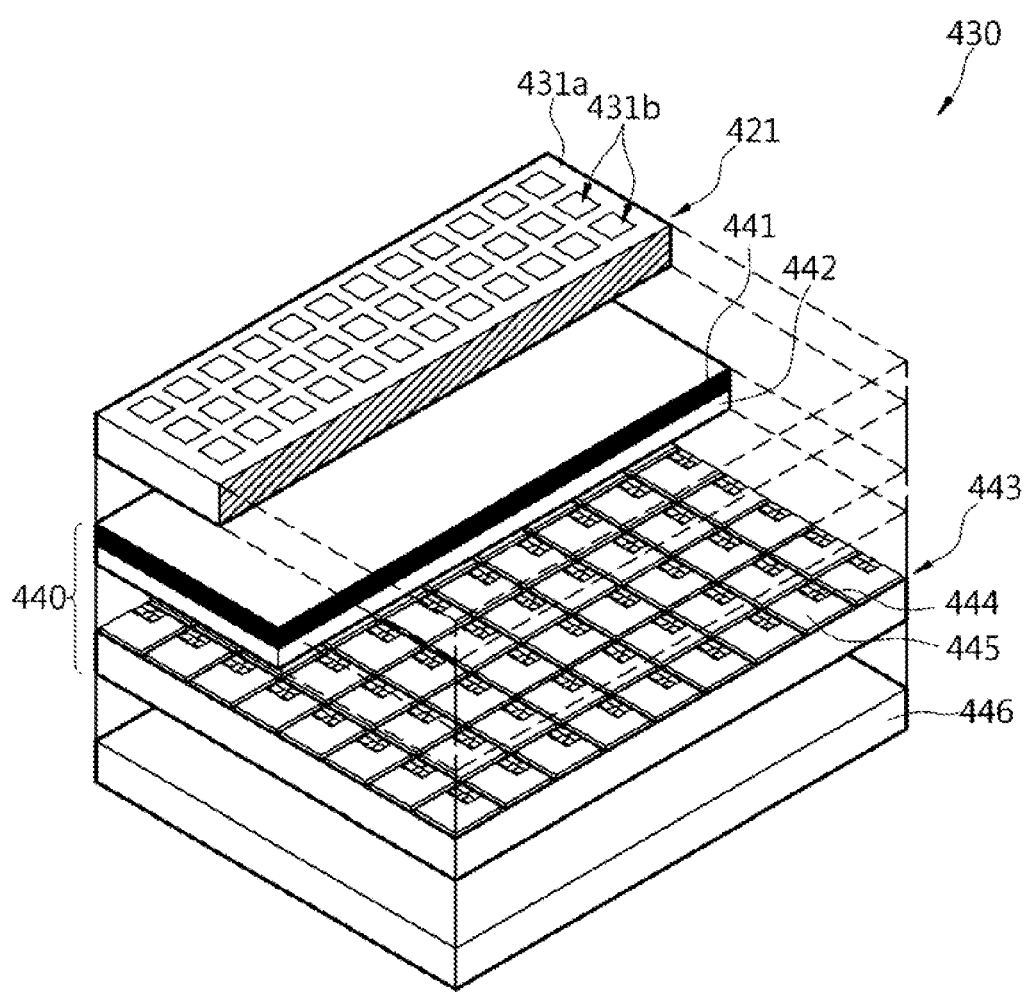
FIG. 7 is a view illustrating an exemplary embodiment of a radiation detecting unit.

FIG. 7 is a view illustrating an exemplary embodiment of the radiation detecting unit. Referring to FIGS. 3, 5 and 7, the radiation detecting unit 430 may include the anti-scatter grid 431, the radiation detecting panel 440, and the substrate 446.

The anti-scatter grid 431 may act to absorb the scattered radiation while the radiation passes through the subject 99 and to allow only the radiation in the proper direction to reach the radiation detecting panel 440. The anti-scatter grid 431 may include a plurality of partitions 431*a* blocking the radiation, and a plurality of penetrating holes 431*b* through which the radiation passes. The partitions 431*a* may be formed of a material such as Pb to absorb the radiation scattered or refracted within the subject 99, and the penetrating holes 431*b* may cause the radiation that is not scattered or refracted to pass.

The radiation detecting panel 440 may receive the radiation, convert the radiation to a corresponding electrical signal, and output the electrical signal. In some exemplary embodiments, the radiation detecting panel 440 may directly convert the radiation to the electrical signal (direct manner), or may generate visible rays according to the radiation and then convert the visible rays into the electrical signal (indirect manner). In a case of the direct manner, the radiation detecting panel 440 may include a first electrode 441 to one surface of which the radiation is applied, a semiconductor material layer 442 provided on the other surface of the first electrode 441 to which the radiation is not applied, and a planar plate 443 provided in contact with the semiconductor material layer 442 at the opposite side of the first electrode 441. Thin film transistors 444 and second pixel electrodes 445 arranged in one or more rows may be provided in the planar plate 443. The polarity of the first electrode 441 may be positive (+) or negative (−), and the polarity of the second electrode 445 may be opposite to that of the first electrode 441. A predetermined bias voltage may be applied between the first electrode 441 and the second electrode 445. Charge-hole pairs generated in the semiconductor material layer 442 according to incidence and absorption of the radiation may move toward the first electrode 441 or the second electrode 445 in accordance with the polarities of the first electrode 441 and the second electrode 445. The second electrode 445 may receive the holes or negative charge transmitted from the semiconductor material layer 442 and output an electrical signal corresponding to the received negative charge. The thin film transistor 444 may read the electrical signal transmitted from the corresponding second electrode 445 to obtain the image data. In some exemplary embodiments, the second electrode 445 and the thin film transistor 444 corresponding to each other may be provided in one CMOS chip. When the radiation detecting unit 430 converts the radiation to the electrical signal in the indirect manner, a phosphor screen outputting visible rays corresponding to the received radiation may be disposed between the anti-scatter grid 431 and the radiation detecting panel, and a photo diode may be disposed in the planar plate 443 instead of the second electrode 445 so as to convert the visible rays to the electrical signal. The radiation detecting panel may include a scintillator outputting predetermined visible photons and a photo diode sensing the visible ray photons in accordance with the radiation. The radiation detecting unit 430 may be a photon counting detector (PCD) in accordance with an exemplary embodiment.

The substrate 446 may be provided on a rear surface of the radiation detecting panel 440. The substrate 446 may be attached to the rear surface of the radiation detecting panel 440 to control various operations of the radiation detecting panel 440 or store image data output from the radiation detecting panel 440.

Referring to FIG. 5, the image data obtained by the radiation detecting unit 430 may be stored in the storage unit 481 temporarily or non-temporarily. The stored image data may be transmitted to the image processing unit 482. The image data obtained by the radiation detecting unit 430 may be directly transmitted to the image processing unit 482. The storage unit 481 may be implemented by a magnetic disk storage device or a semiconductor storage device. The image processing unit 482 may perform image correction by adjusting the contrast or bauthorityness on the basis of the image data. In some exemplary embodiments, the image processing unit may generate a real-time image, perform image processing such as DSA processing, and generate a three-dimensional image. The image processing unit 482 may include a processor implemented as a semiconductor chip. The image processing unit 482 may be implemented by the real-time processing unit 100 or the non-real-time processing unit 200.

The radiation imaging unit 400 may further include a driving unit 490 as shown in FIG. 3. The driving unit 490 may move the radiation applying unit 410 or the radiation detecting unit 430 to cause the radiation applying unit 410 to apply the radiation to several positions of the subject 99 or to cause the radiation detecting unit 430 to detect the radiation that has passed through the subject 99. The driving unit 490 may include an arm, which may have various shapes depending on the apparatus. In addition, the driving unit 490 may include rails, wheels, motors, or the like, and may move the wheels along the rails using power from the motors to cause the radiation applying unit 410 or the radiation detecting unit 430 coupled with the wheels to move. In addition, the driving unit 490 may move the radiation applying unit 410 or the radiation detecting unit 430 through an action of the activator. The driving unit 490 may use a hydraulic pressure to move the radiation applying unit 410 or the radiation detecting unit 430 if necessary.

Hereinafter, the fluoroscopy apparatus will be described as an example of the radiation imaging unit 400 with reference to FIGS. 8 to 10.

Figure 8:
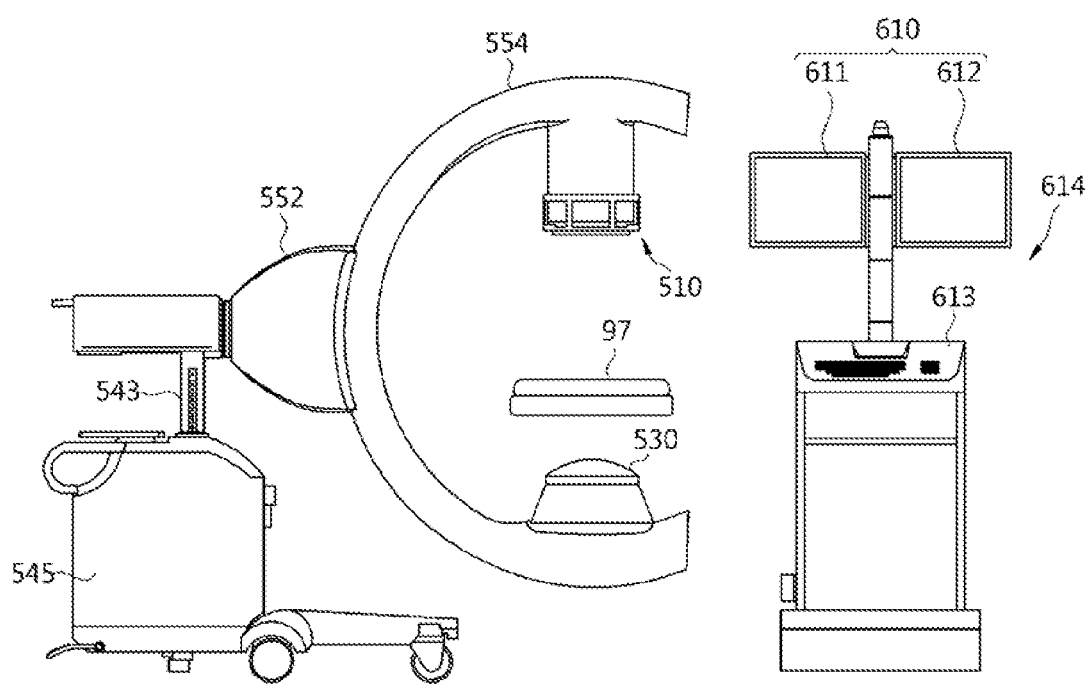
FIG. 8 is a view illustrating an exemplary embodiment of a fluoroscopy apparatus.
Figure 9:
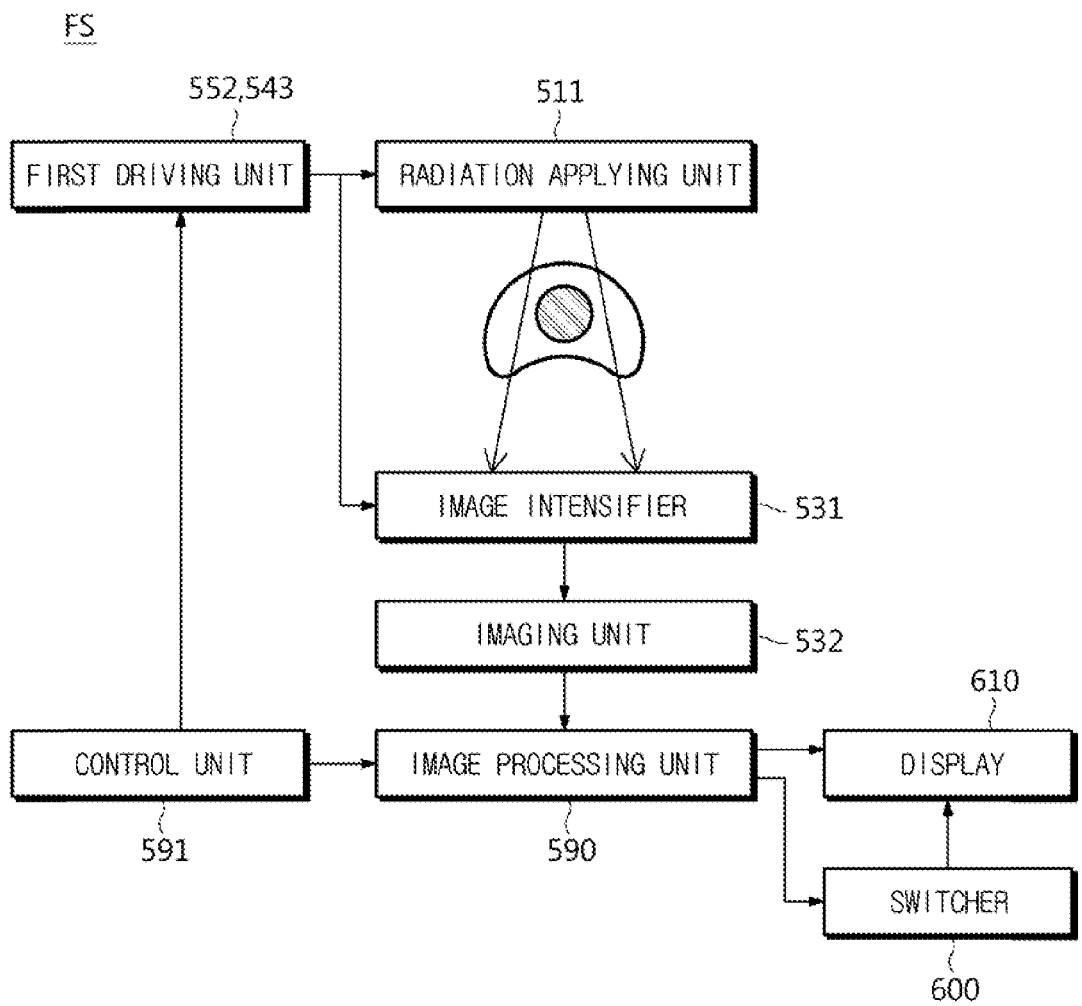
FIG. 9 is a block diagram illustrating an exemplary embodiment of a fluoroscopy apparatus.
Figure 10:
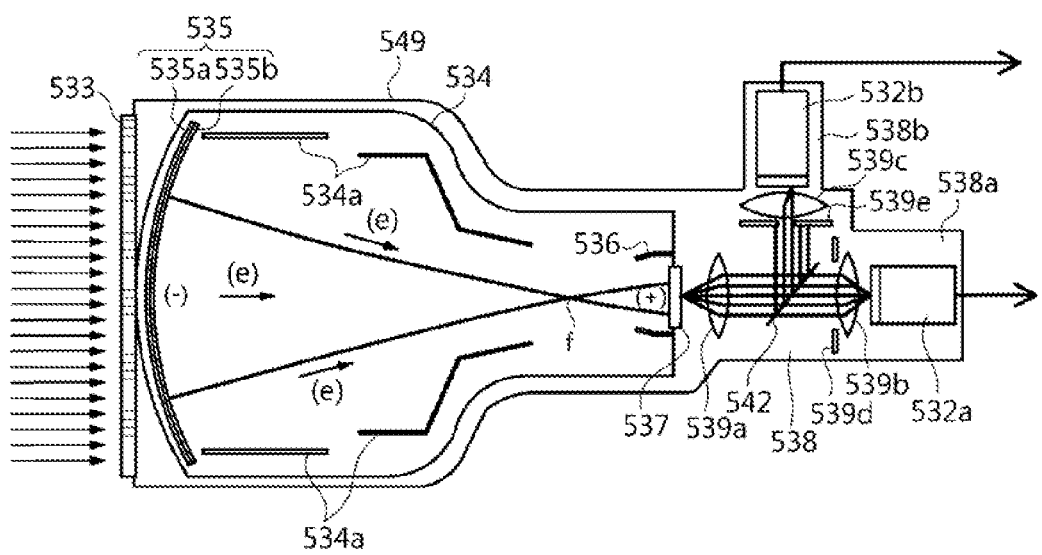
FIG. 10 is a view illustrating an exemplary embodiment of an image intensifier.

FIG. 8 is a view illustrating an exemplary embodiment of the fluoroscopy apparatus, and FIG. 9 is a block diagram illustrating an exemplary embodiment of the fluoroscopy apparatus. As shown in FIG. 8, the fluoroscopy (FS) apparatus may include a radiation applying module 510 that applies radiation to the subject, a radiation detecting module 530 that receives radiation that has passed through the subject and outputs image data according to the received radiation, a frame 554 in which the radiation applying module 510 and the radiation detecting module 530 are installed, driving units 552 and 543 that drive the frame 554 according to the direction or position in which the radiation is applied, a main body 545 in which various components associated with operations or the like of respective apparatuses are stored, a workstation main body 614 in which various components for controlling operations of the respective apparatuses or performing the image processing are stored, an input unit 613 that receives an instruction from the user, and displays 610, 611, and 612 that display radiation images to the user. In addition, as shown in FIG. 9, the fluoroscopy (FS) apparatus may include an imaging unit 532 imaging photons output from the image intensifier 531, an image processing unit 590 that performs the image processing on the image data obtained by the imaging unit 532, a switcher 600 that distributes the image-processed images to respective displays 611 and 612, and a control unit 591 that controls operations of respective components of the fluoroscopy (FS) apparatus.

The radiation applying module 510 may include a radiation applying unit 511 that applies the radiation to the subject held on the stand 97. The radiation applying unit 511 may include a radiation tube and a collimator for filtering the radiation applied from the radiation tube as shown in FIG. 6. The radiation tube and the collimator of the radiation applying module 510 may be the same as those described in the DR imaging apparatus or may be partially modified.

The radiation detecting module 530 may include an image intensifier 531 and an imaging unit 532. The image intensifier 531 may emit photons corresponding to the incident radiation, and the imaging unit 532 may receive or detect the photons to obtain the image data. FIG. 10 is a view illustrating an exemplary embodiment of the image intensifier. As shown in FIG. 10, the image intensifier 531 may include an anti-scatter grid 533, a tubular body 534, a radiation-electron converting unit 535, an anode 536, an electron-light converting unit 537, an optical passage 538, lenses 539a to 539c, and a housing 549.

The anti-scatter grid 533 may act to absorb the scattered radiation while the radiation passes through the subject and to allow only the radiation in the proper direction to reach the radiation-electron converting unit 535 of the tubular body 534. The anti-scatter grid 533 may include a plurality of partitions formed, for example, of Pb for blocking the radiation and penetrating holes through which the radiation that is not scattered pass. The radiation that has passed through penetrating holes may reach the radiation-electron converting unit 535. The anti-scatter grid 533 may be provided in the direction of the radiation-electron converting unit 535 of the tubular body 534.

Various components such as the radiation-electron converting unit 535, the anode 536, and the electron-light converting unit 537 may be stably fixed in the tubular body 534, and electrons (e) moving within the tubular body 534 may be focused toward the anode 536 and shielded from leaking out. The tubular body 534 may have a substantially cylindrical shape. The tubular body 534 have the cylindrical shape such that a diameter thereof in a direction in which the radiation-electron converting unit 535 is disposed toward the cathode (−) is greater than a diameter thereof in a direction in which the electron-light converting unit 537 is disposed toward the anode (+) as shown in FIG. 10. The cathode (−) portion in which the radiation-electron converting unit 535 of the tubular body 534 is disposed may have a lens shape protruding convexly in the direction in which the radiation is applied. Electrons may move toward the anode 536 within the tubular body 534 to focus on the focusing point (f) that is a point arranged near the anode 536. A focusing electrode 534a may be further provided within the tubular body 534. The focusing electrode 534a may guide the electrons (e) moving toward the anode 536 to be focused on the focusing point (f).

The radiation-electron converting unit 535 may be provided toward the cathode (−) in the tubular body 534. The radiation-electron converting unit 535 may include a fluorescent plate 535a emitting photons corresponding to the incident radiation after the radiation is incident, and a photocathode plate 535b emitting electrons (e) corresponding to the photons emitted from the fluorescent plate 535a. The fluorescent plate 535a and the photocathode plate 535b may have a shape corresponding to the lens shape of the cathode (−) portion of the tubular body 534. Accordingly, the electrons (e) emitted from the photocathode plate 535b may move to be focused on the focusing point (f) within the tubular body 534.

The anode 536 may guide a movement direction of the electrons (e). The electrons (e) may be focused around the anode 53 while moving toward the anode 536 in accordance with the polarity of the electrons (e). The anode 536 may accelerate the moving electrons (e). The electron-light converting unit may be provided around the anode 536. The electron-light converting unit 537 may emit visible photons corresponding to the incident electrons (e) into the optical passage 538. The electron-light converting unit 537 may include an output phosphor. Lights emitted into the optical passage 538 may be refracted by a first lens 539a and propagate in parallel with each other. The output photons may form an image. The output photons may be received by the imaging unit 532, and the imaging unit 532 may output and store electrical signals corresponding to the received photons to obtain image data.

A reflective mirror 542 for reflecting the emitted photons in various directions may be provided within the optical passage 538. The reflective mirror 542 may transmit some of the output photons to a first optical passage 538a in which a first imaging unit 532a is provided, and transmit some thereof to a second optical passage 538b in which a second imaging unit 532b is provided. Accordingly, a plurality of types of image data may be obtained. The first optical passage 538a and the second optical passage 538b may be provided with a second lens 539b and a third lens 539c, respectively, focusing transmitted lights. Lights focused on the second lens 539b and the third lens 539c may be transmitted to the first imaging unit 532a and the second imaging unit 532b. The first optical passage 538a and the second optical passage 538b may be provided with a first aperture 539d and a second aperture 539e for adjusting an amount of light incident on the first imaging unit 532a and the second imaging unit 532b, respectively.

The housing 549 may have the anti-scatter grid 533, the tubular body 534, the radiation-electron converting unit 535, the anode 536, the electron-light converting unit 537, the optical passage 538, and the lenses 539a to 539c stored therein, reliably fixing them, and preventing damage resulting from external stimuli. The housing 549 may have a shape corresponding to the shape of the tubular body 534 or the optical passage 538.

The imaging unit 532 may receive photons, and generate and store electrical signals corresponding to the received photons, thereby obtaining image data. The imaging unit 532 may include an image sensor having a plurality of imaging elements, and a charge coupled device (CCD) or a complementary metal-oxide semiconductor (CMOS) may be used as the imaging elements.

At least one of the radiation applying module 510 and the radiation detecting module 520 may be provided in the frame 594. The frame 594 may include a "C"-shaped frame. The radiation applying module 510 and the radiation detecting module 520 may be provided to correspond to each other at both ends of the "C"-shaped frame.

The driving units 592 and 593 may perform rotation of the frame 594 or vertical or horizontal movement of the frame. The driving units 592 and 593 may drive the frame 594 using supports, motors, rails, wheels, or the like.

Various components such as a semiconductor chip and a printed circuit board may be stored in the main body 595. The semiconductor chip stored in the main body 595 may perform functions of the control unit 591. In this case, the control unit 591 may be set to only control operations of the driving units 592 and 593. Some of the driving units 592 and 593 may be stored in the main body 595.

Various components such as a semiconductor chip and a printed circuit board may be stored in the workstation main body 614, and the semiconductor chip stored in the workstation main body 614 may perform functions of the control unit 591. In this case, the control unit 591 may analyze an instruction input from the user to generate a control signal, or may control the image processing and the display 610 such that the processing is displayed on the display. The display 610 or the input unit 613 may be provided in the workstation main body 614.

The image processing unit 590 may perform the image processing on the image data obtained by the imaging unit 532, and may be implemented by the real-time processing unit 100 or the non-real-time processing unit 200 as described above. The control unit 591 may control operations of the driving units 592 and 593, the radiation applying unit 511, or the image processing unit 590, and may be implemented by the real-time processing unit 100, the non-real-time processing unit 200, or the central controller 300 as described above.

The DR imaging apparatus and the fluoroscopy apparatus have been described as specific examples of the radiation imaging unit 400 so far. However, the apparatus that may be used as the radiation imaging unit 400 is not limited to the DR imaging apparatus or the fluoroscopy apparatus described above. A CT apparatus, a mammography apparatus, or a SPECT apparatus may also be used as the radiation imaging unit 400 as described above or in a slightly different manner.

Hereinafter, the real-time processing unit, the non-real-time processing unit, and the central controller will be described with reference to FIGS. 11 to 13.

Figure 11:
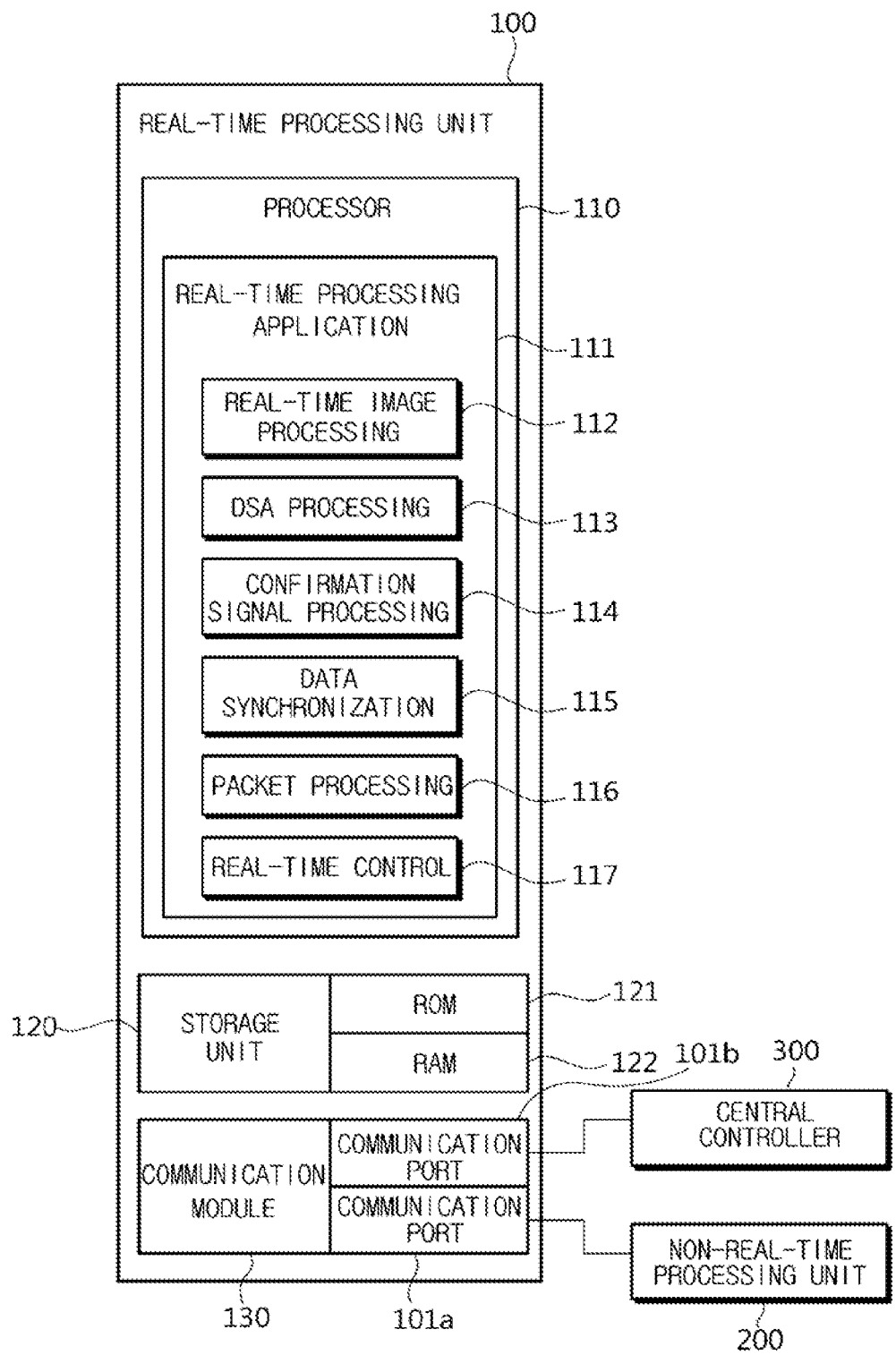
FIG. 11 is a block diagram illustrating an exemplary embodiment of a real-time processing unit.

FIG. 11 is a block diagram illustrating an exemplary embodiment of the real-time processing unit.

The real-time processing unit 100 may perform the real-time image processing on the image data obtained by the radiation imaging unit 400 or the real-time control of the radiation imaging unit 400. In particular, the real-time processing unit 100 may perform operations of at least one of real-time image processing, DSA processing, confirmation signal processing, data synchronization, packet processing, and real-time control of the radiation imaging unit 400. Referring to FIG. 11, the real-time processing unit 100 may include a processor 110, a storage unit 120, and a communication module 130.

The processor 110 may calculate and process various data necessary for operations of the real-time processing unit 100 or may control operations of each component of the real-time processing unit 100. The processor 110 may load and drive a real-time processing application 111. In this case, the application may be a set of a series of computer programs. The real-time processing application 111 may include a plurality of programs 112 to 117 for performing various tasks. The programs mean a set of instructions for causing the apparatus such as a computer to process the tasks. In particular, the real-time processing application 111 may include at least one program of a real-time image processing program 112, a DSA processing program 113, a confirmation signal processing program 114, a data synchronization program 115, a packet processing program 116, and a real-time control program 117 of the radiation imaging unit 400. The real-time processing application 111 may include all of the real-time image processing program 112, the DSA processing program 113, the confirmation signal processing program 114, the data synchronization program 115, the packet processing program 116, and the real-time control program 117 of the radiation imaging unit 400, or may include only some of them. For example, the real-time control program 117 may be omitted from the real-time processing application 111. Each program of the real-time processing application 111 may be organically associated and executed, or may be executed separately. For example, the confirmation signal processing program 114 may be executed in connection with execution of the real-time image processing program 112. In addition, for example, the real-time image processing program 112 and the real-time control program 117 may be executed independently from each other.

The real-time processing unit 100 may generate a real-time image on the basis of the image data that is raw data transmitted from the radiation imaging unit 400 in accordance with execution of the real-time image processing program 112. The generated real-time image may be displayed by the display 610. The real-time image may be displayed by the first display 611. In addition, the real-time processing unit 100 may perform the image processing such as correction of the real-time image generated in accordance with execution of the real-time image processing program 112. Correction of the real-time image may include correction of contrast, bauthorityness, or sharpness of the real-time image, removal of noise of the real-time image, and so forth. Additionally, correction of the real-time image may include any corrections that can be processed in real time. The image processing for the real-time image may be performed for all sections of the real-time image or some sections of the real-time image.

The real-time processing unit 100 may perform the DSA processing using the DSA processing program 112. The DSA processing may be a method of performing subtraction processing using an image imaged before injecting the contrast medium into the subject 99 and an image imaged after injecting the contrast medium into the subject 99 to extract specific portions. According to the DSA processing, blood vessels within the human body serving as the subject 99 in which the contrast medium moves may be more clearly extracted. The real-time processing unit 100 may perform the DSA processing on a plurality of images in accordance with operations of the DSA processing program 112 to generate a new contrast medium image with the extracted specific portion. In addition, the real-time processing unit 100 may synthesize the new contrast medium image with an existing image to generate a new synthesized image through the DSA processing program 112 if necessary.

The real-time processing unit 100 may generate a response signal corresponding to the confirmation signal transmitted from the non-real-time processing unit 200 or the central controller 300 through the confirmation signal processing program 114. The confirmation signal processing program 114 may be immediately executed to generate the response signal quickly when the confirmation signal is received from the non-real-time processing unit 200 or the central controller 300. In addition, the confirmation signal processing program 114 may be executed to generate the response signal after a predetermined time has elapsed after the receiving confirmation signal from the non-real-time processing unit 200 or the central controller 300. The confirmation signal processing program 114 may periodically generate the response signal at a preset timing or interval. The response signal may be transmitted to the non-real-time processing unit 200 or the central controller 300 via the communication module 130. The response signal may be transmitted to the apparatuses 200 and 300 that have transmitted the confirmation signal. In some exemplary embodiments, the response signal may be periodically transmitted to the non-real-time processing unit 200 or the central controller 300 at a preset timing or interval. In this case, the response signal to be transmitted may be packetized by the packet processing program 116 and then transmitted to the outside via the communication module 130.

The real-time processing unit 100 may transmit the real-time image and associated data obtained using the data synchronization program 115 to the non-real-time processing unit 200. The non-real-time processing unit 200 may store the received real-time image and the associated data. For example, the real-time processing unit 100 may execute the data synchronization program 115 to cause the real-time image or the contrast medium image stored in the real-time processing unit 100 to be transmitted to the non-real-time processing unit 200. In this case, the associated data may include detailed information on the real-time image or a history associated with the real-time image processing. The detailed information on the real-time image may include various information such as a generation time and a correction time of the real-time image, and a manufacturer or a model of the radiation imaging unit 400. The real-time processing unit 100 may transmit the real-time image and the associated data to the non-real-time processing unit 200 in accordance with a constant period or in an arbitrary time while the real-time image processing is performed. Accordingly, the non-real-time processing unit 200 may have the same data as the data of the real-time processing unit 100. It is thus possible to provide the user with data already processed in the real-time processing unit 100, for example, the already generated real-time image and the contrast medium image, even when a failure occurs in the real-time processing unit 100. The data already processed in the real-time processing unit 100 may be used by the non-real-time processing unit 200. In addition, when a change occurs in various settings of the real-time processing unit 100 due to execution of the data synchronization program 115, the real-time processing unit 100 may transmit the changed settings to the non-real-time processing unit 200 to be stored in the storage device of the non-real-time processing unit 200. It is thus possible for the real-time processing application 240 stored in a storage unit 220 to be synchronized with the real-time processing application 11 of the real-time processing unit 100, and the non-real-time processing unit 200 can perform the real-time image processing or the like with the same settings when a failure occurs in the real-time processing unit 100.

The real-time processing unit 100 may packetize data to be transmitted to the outside through the packet processing program 116. The real-time processing unit 100 may packetize the data in the form of a datagram including information for determining the path from the sender to the receiver. The datagram may include information on the receiver who receives the data and the sender that has transmitted the data. For example, Internet protocol (IP) addresses of the sender and the receiver may be stored in the header of the datagram. The sender address, the receiver address, and the packet order may be sequentially stored in the header of the datagram.

The data to be transmitted to the outside may include a failure occurrence notification signal to be transmitted to the non-real-time processing unit 200 or the central controller 300, a response signal to a confirmation signal, various data to be transmitted to the non-real-time processing unit 200, control signals to be transmitted to respective components, or the like.

The real-time processing unit 100 may control real-time operations of the radiation imaging unit 400 through the real-time control program 117. When the real-time control program 117 is executed, the real-time processing unit 100 may generate control signals for the driving unit 490 or the power source 492 of the radiation imaging unit 400 and transmit the generated control signals to the corresponding components via the communication port 101.

The processor 110 may be implemented by a semiconductor chip. The processor 110 may be implemented by a central processing unit (CPU) or may be implemented by a graphic processing unit (GPU). The GPU may include a semiconductor chip such as a graphic chip.

The storage unit 120 may store various data or settings. The storage unit 120 may include volatile or non-nonvolatile storages such as a ROM 121 or a RAM 122. In addition, the storage unit 120 may include storages for recording data using the magnetic field such as a magnetic disk or a magnetic tape, and storage media for recording data using an optical method such as a CD or a DVD.

The communication module 130 may transmit and receive data to and from an external apparatus via a wired communication network or a wireless communication network. When communication is performed via the wired communication network, the communication module 130 may include a LAN card. When communication is performed via the wireless communication network, the communication module 130 may include an antenna and a wireless communication chip. The communication module 130 may include a plurality of communication ports 101a and 101b. Each of the plurality of communication ports 101a and 101b may be connected to a different apparatus. For example, the first communication port 101a may be connected to the non-real-time processing unit 200, and the second communication port 101b may be connected to the central controller 300. Terminals of a UTP cable or general-purpose serial bus terminals may be inserted into the communication ports 101a and 101b.

Figure 12:
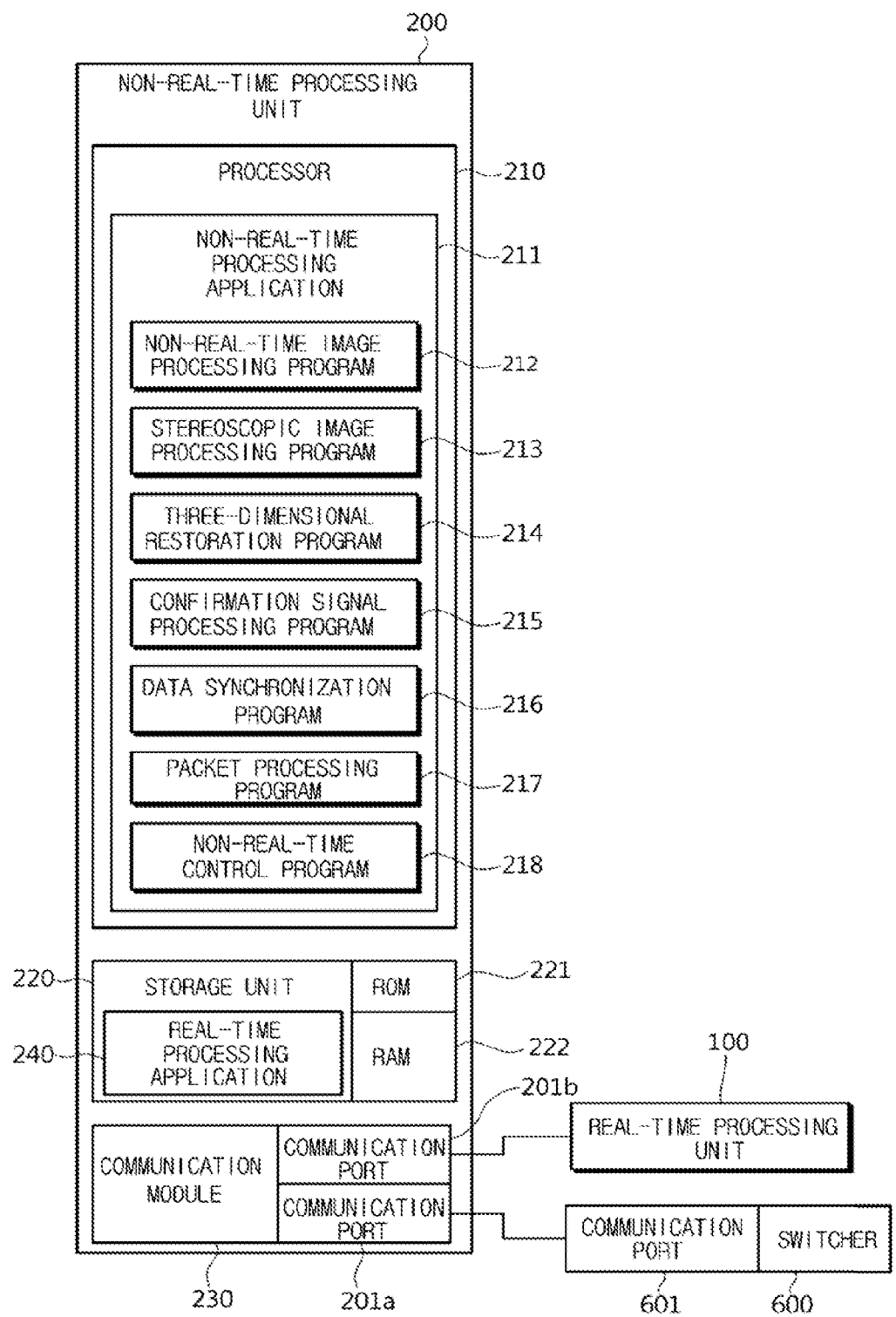
FIG. 12 is a block diagram illustrating an exemplary embodiment of a non-real-time processing unit.

FIG. 12 is a block diagram illustrating an exemplary embodiment of the non-real-time processing unit.

The non-real-time processing unit 200 may perform the non-real-time image processing on the image data obtained by the radiation imaging unit 400 or the non-real-time control of the radiation imaging unit 400. In particular, the non-real-time processing unit 200 may perform operations of at least one of the non-real-time image processing, the stereoscopic image processing, the volume data processing, the confirmation signal processing, the data synchronization, the packet processing, and the real-time control of the radiation imaging unit 400. Referring to FIG. 12, the non-real-time processing unit 200 may include a processor 210, a storage unit 220, and a communication module 230.

The processor 210 may control general operations of the non-real-time processing unit 200. The processor 210 may calculate and process various data necessary for operations of the non-real-time processing unit 200 or may control operations of each component of the non-real-time processing unit 200. The processor 210 may load and drive a non-real-time processing application 211. The non-real-time processing application 211 may include a plurality of programs 212 to 218 for performing various tasks. In particular, the non-real-time processing application 211 may include at least one program of a non-real-time image processing program 212, a stereoscopic image processing program 213, a three-dimensional restoration program 214, a confirmation signal processing program 215, a data synchronization program 216, a packet processing program 217, and a non-real-time control program 218. The non-real-time processing application 211 may include some or all of these. For example, the non-real-time control program 218 may be omitted from the non-real-time processing application 211. Each program of the non-real-time processing application 211 may be organically associated and executed, or may be executed separately.

The non-real-time processing unit 200 may execute the non-real-time image processing program 212 of the non-real-time application 211 to generate a non-real-time image on the basis of the image that is raw data transmitted from the radiation imaging unit 400. The generated non-real-time image may be displayed by the display 610. In some exemplary embodiments, the non-real-time image may be displayed by the second display 612. Correction of contrast, bauthorityness, or sharpness may be performed on the non-real-time image, or the image processing such as removal of noise of the real-time image may be performed in accordance with execution of the real-time image processing program 112. Additionally, various image processing may be performed on the non-real-time image. The image processing of the non-real-time image may also be performed for all sections of the image or some sections of the image.

The non-real-time processing unit 200 may use the stereoscopic image processing program 212 to generate a stereoscopic image. The generated stereoscopic image may be a stereoscopic image that can be stereoscopically displayed in accordance with stereography using polarizing eyeglasses or shutter eyeglasses, or a stereoscopic image that can be stereoscopically displayed in accordance with a lenticular method. The generated stereoscopic image may be provided to the user via the predetermined display 610 capable of representing the stereoscopic image.

The non-real-time processing unit 200 may execute the three-dimensional restoring program 213 to generate a three-dimensional image using volume data. In particular, when a large amount of image data is input, the three-dimensional restoring program may restore the three-dimensional image for the subject 99 on the basis of the image data. The three-dimensional image may also be displayed by the display 610.

The non-real-time processing unit 200 may generate a confirmation signal for confirming whether the real-time processing unit 100 operates according to the confirmation signal processing program 215. The generated confirmation signal may be transmitted to the real-time processing unit 100 via the second communication port 201*b*. The confirmation signal to be transmitted may be packetized by the packet processing program 217 and then transmitted. In addition, the non-real-time processing unit 200 may generate a response signal corresponding to the confirmation signal transmitted from the central controller 300 through the confirmation signal processing program 215. When the confirmation signal is received, the confirmation signal processing program 215 may be immediately executed to generate the response signal quickly, or may be executed to generate the response signal after a predetermined time has elapsed after receiving the confirmation signal. The confirmation signal processing program 215 may periodically generate the response signal or at a preset timing or intervals. In this case, the response signal may be periodically transmitted or transmitted at a preset timing or intervals to the central controller 300. The response signal may be packetized by the packet processing program 217 and then transmitted.

The non-real-time processing unit 200 may use the data synchronization program 216 to receive the real-time image and associated data obtained by the real-time processing unit 100 and store them in the storage unit 220. Accordingly, the same data as the data of the real-time processing unit 100 may be stored in the storage device of the non-real-time processing unit 200. In addition, the non-real-time processing unit 200 may receive the changed settings of the real-time processing unit 100 and store the changed settings in the storage unit 220. Accordingly, the real-time processing application 240 stored in the storage unit 220 may be synchronized with the real-time processing application 111 of the real-time processing unit 100. It is thus possible for the non-real-time processing unit 200 to operate in accordance with the same data and settings as the real-time processing unit 100 even when a failure occurs in the real-time processing unit 100 and the real-time processing unit 100 is not operable.

The non-real-time processing unit 200 may execute the packet processing program 217 to packetize data to be transmitted to the outside. The non-real-time processing unit 200 may packetize the data to be transmitted to the outside through the packet processing program 217 in the form of a datagram including a destination to which the data is to be transmitted and a source. The data to be transmitted to the outside may include a failure occurrence notification signal to be transmitted to the central controller 300, a response signal to a confirmation signal, a confirmation signal to be transmitted to the real-time processing unit 100, or a control signal of the radiation imaging unit 400.

The non-real-time processing unit 200 may control non-real-time operations of the radiation imaging unit 400 according to the non-real-time control program 218. When the non-real-time control program 218 is executed, the non-real-time processing unit 200 may generate a control signal for the driving unit 490 or the power source 492 of the radiation imaging unit 400 and transmit the generated control signal to the corresponding component via the communication port 201.

The processor 210 described above may be implemented by a semiconductor chip or the like. The processor 110 may be implemented by least one of a CPU and a GPU.

The storage unit 220 may store various data or settings temporarily or non-temporarily. The storage unit 220 may include various kinds of storages and media such as volatile or non-volatile storages such as a ROM 221 or a RAM 222, magnetic disk storages, magnetic tape storages, a CD, or a DVD. The storage unit 220 may store the real-time processing application 240. The real-time processing application 240 may be the same kind of application as the real-time processing application 111 being executed by the real-time processing unit 100. The real-time processing application 240 stored in the storage unit 220 may be synchronized with the real-time processing application 111 of the real-time processing unit 100 in accordance with execution of the data synchronization program 115 of the real-time processing unit 100 and the data synchronization program 216 of the non-real-time processing unit 200.

The communication module 230 may transmit and receive data to and from an external apparatus via a wired communication network or a wireless communication network. When communication is performed via the wired communication network, the communication module 230 may include a LAN card. When communication is performed via the wireless communication network, the communication module 230 may include an antenna and a wireless communication chip. The communication module 230 may include a plurality of communication ports 201*a* and 201*b*. Each of the plurality of communication ports 201*a* and 201*b* may be connected to a different apparatus in the same way as described above. For example, the first communication port 201*a* of the communication module 230 may be connected to the real-time processing unit 100, and the second communication port 201*b* of the communication module 230 may be connected to the switcher 600. Terminals of the UTP cable or general-purpose serial bus terminals may be inserted into the communication ports 101*a* and 101*b*.

As shown in FIGS. 2 and 3, the real-time processing unit 100 and the non-real-time processing unit 200 may be implemented by respective workstations that are physically independent from each other. In some exemplary embodiments, one workstation may perform functions of the real-time processing unit 100 and the non-real-time processing unit 200. In addition, a plurality of workstations may perform the function of the real-time processing unit 100. Similarly, a plurality of workstations may perform the function of the non-real-time processing unit 200. The real-time processing unit 100 and the non-real-time processing unit 200 may further include various components that may be considered by those skilled in the art such as housings or various interface apparatuses in addition to the apparatuses described above.

The central controller 300 may control general operations of the radiographic imaging apparatus 10. For example, the central controller 300 may control the real-time processing unit 100, the non-real-time processing unit 200, the radiation imaging unit 400, the switcher 600, and so forth by transmitting control signals to the real-time processing unit 100, the non-real-time processing unit 200, the radiation imaging unit 400, the switcher 600, and so forth. In addition, the central controller 300 may sense whether a failure occurs in the real-time processing unit 100, and when a failure occurs, control the non-real-time processing unit 200 such that the non-real-time processing unit has the real-time control authority and performs the real-time processing. The central controller 300 may be implemented by a general computer in which a predetermined application is installed, or may be implemented by a separately manufactured apparatus for controlling the radiographic imaging apparatus 10.

Figure 13:
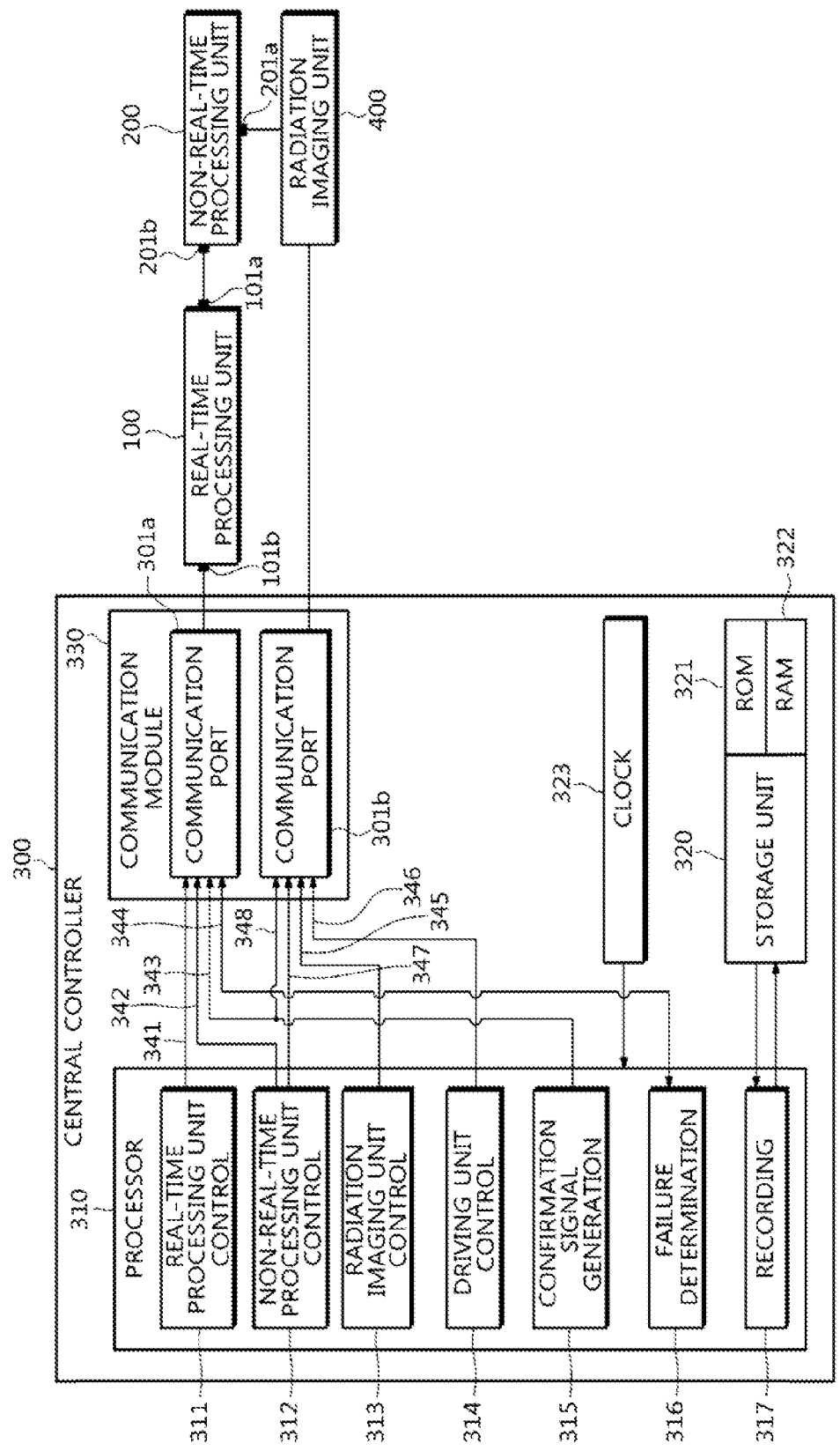
FIG. 13 is a block diagram illustrating an exemplary embodiment of a central controller.

FIG. 13 is a block diagram illustrating an exemplary embodiment of the central controller. Referring to FIG. 13, the central controller 300 may include a processor 310, a storage unit 320, and a communication module 330.

The processor 310 may perform at least one function of real-time processing unit control 311, non-real-time processing unit control 312, radiation imaging control unit control 313, driving unit control 314, generation of a confirmation signal 315, failure determination 316, and recording 317. The processor 310 may perform all functions 311 to 317 described above as shown in FIG. 13, and or some of the functions may be omitted.

In particular, the processor 310 of the central controller 300 may generate various control instructions associated with operations of the real-time processing unit 100 and transmit the generated control instructions to the real-time processing unit 100 (311). For example, the processor 310 may transmit an operation start instruction or an operation stop instruction to the real-time processing unit 100 to control the real-time processing unit such that the real-time processing unit 100 starts or stops operation. In this case, the processor 310 may transmit the operation stop instruction to the real-time processing unit 100 and take the real-time processing authority away from the real-time processing unit when the processor determines that a failure occurs in the real-time processing unit 100. In some exemplary embodiments, the real-time processing unit 100 may not operate under control of the central controller 300. In such cases, the processor 310 may not generate various control instructions associated with operations of the real-time processing unit 100.

The processor 310 may transmit the control signal 341 to the real-time processing unit 100 via a first communication port 301a connected with the communication port 101b of the real-time processing unit 100 via a cable or the like. In some exemplary embodiments, the processor 310 may transmit the control signal via a different second communication port 301b. In such cases, the control signal is transmitted to the real-time processing unit 100 via at least one of the radiation imaging unit 400, the switcher 600, and the non-real-time processing unit 200. The processor 310 may transmit the control signal to the real-time processing unit 100 using both of the first communication port 301a and the second communication port 301b. In this case, the real-time processing unit 100 may receive the control signal in both directions.

In addition, the processor 310 of the central controller 300 may generate various control instructions associated with operations of the non-real-time processing unit 200 and transmit the generated control instructions to the non-real-time processing unit 200 (312). For example, the processor 310 may transmit the real-time processing authority or the instruction for activating the real-time processing authority to the non-real-time processing unit 200 to cause the non-real-time processing unit 200 to perform the real-time image processing. According to an exemplary embodiment, the processor 310 may transmit the real-time processing author- ity or the instruction for activating the real-time processing authority to the non-real-time processing unit 200 when a failure occurs in the real-time processing unit 100. In addition, the processor 310 may control start and stop of operations of the non-real-time processing unit 200 by transmitting the operation start instruction or the operation stop instruction to the non-real-time processing unit 200. In some exemplary embodiments, the non-real-time processing unit 200 may not operate under control of the central controller 300. In such cases, the processor 310 may not generate control instructions associated with operations of the non-real-time processing unit 200.

Referring to FIG. 13, the central controller 300 may not be directly connected to either of the communication ports 201a and 201b of the non-real-time processing unit 200. In this case, the processor 310 may transmit a control signal 342 to the real-time processing unit 100 via the first communication port 301a connected with the communication port 101b of the real-time processing unit 100 via a cable or the like and then transmit the control signal 342 to the non-real-time processing unit 200 via the real-time processing unit 100. In addition, the processor 310 may transmit a control signal 347 to the radiation imaging unit 400 via the second communication port 301b connected with the radiation imaging unit 400 and then transmit the control signal to the non-real-time processing unit 200 via the radiation imaging unit 400, the switcher 600, and so forth. The processor 310 may transmit the control signal to the non-real-time processing unit 200 using both of the first communication port 301a and the second communication port 301b. In this case, the non-real-time processing unit 200 may receive the control signal in both directions.

The processor 310 may generate a control signal for controlling the radiation imaging unit 400 and then transmit the generated control signal to the radiation imaging unit 400 (313). The control signal may include a signal for controlling the power source 492 of the radiation imaging unit 400. Referring to FIG. 13, the processor 310 may transmit a control signal 345 for controlling the radiation imaging unit 400 to the radiation imaging unit 400 via the communication port of the radiation imaging unit 400 or the second communication port 301b connected with the adaptor 493 via a cable or the like. The processor 310 may also transmit the control signal to the real-time processing unit 100 via the first communication port 301a connected with the communication port 101b of the real-time processing unit 100 via a cable or the like and then transmit the control signal to the radiation imaging unit 400 via the real-time processing unit 100, the non-real-time processing unit 200, and so forth. The processor 310 may transmit the control signal to the radiation imaging unit 400 via both of the first communication port 301a and the second communication port 301b. In this case, the radiation imaging unit 400 may receive the control signal in both directions.

The processor 310 may generate a control signal for controlling the driving unit 490 of the radiation imaging unit 400 and the transmit the generated control signal to the driving unit 490 of the radiation imaging unit 400. The control signal may include a signal for controlling movement of at least one of the radiation applying unit 410 and the radiation detecting unit 430 of the radiation imaging unit 400. The processor 310 may transmit a control signal 346 for controlling the radiation imaging unit 400 to the driving unit 490 via the second communication port 301b connected with the communication port of the adaptor 491 of the driving unit 490 via a cable or the like. The processor 310 may also transmit the control signal the real-time processing unit 100 via the first communication port 301*a* connected with the communication port 101*b* of the real-time processing unit 100 via a cable or the like and then transmit the control signal the driving unit 490 via the real-time processing unit 100, the non-real-time processing unit 200, and so forth. In this case, the control signal may be transmitted to the driving unit 490 via the radiation detecting panel 440 and the anti-scatter grid 431 of the radiation imaging unit 400. The processor 310 may transmit the control signal to the driving unit 490 via both of the first communication port 301*a* and the second communication port 301*b*. In this case, the driving unit 490 may receive the control signal in both directions.

The processor 310 may periodically generate a confirmation signal for confirming whether at least one of the real-time processing unit 100 and the non-real-time processing unit 200 operates normally at a preset timing or interval and then transmit the generated control signal to at least one of the real-time processing unit 100 and the non-real-time processing unit 200 (315). The processor 310 may generate the confirmation signal in accordance with a predetermined period, or may generate the confirmation signal in an arbitrary time. The confirmation signals transmitted to the real-time processing unit 100 and the non-real-time processing unit 200 may be the same or different. When the confirmation signal is given in the form of datagram, the receiver address of the confirmation signal transmitted to the real-time processing unit 100 is different from that of the confirmation signal transmitted to the non-real-time processing unit 200.

The processor 310 may transmit a confirmation signal 343 to the real-time processing unit 100 via the first communication port 301*a* connected with the communication port 101*b* of the real-time processing unit 100 via a cable or the like. In some exemplary embodiments, the processor 310 may also transmit the confirmation signal via the different second communication port 301*b*. When the central controller 300 is not directly connected to either of the communication ports 201*a* and 201*b* of the non-real-time processing unit 200, the processor 310 may transmit the confirmation signal to the real-time processing unit 100 via the first communication port 301*a* connected with the communication port 101*b* of the real-time processing unit 100 via a cable or the like, and the real-time processing unit 100 may transmit the received confirmation signal to the non-real-time processing unit 200. In addition, the processor 310 may transmit the confirmation to the non-real-time processing unit 200 via the radiation imaging unit 400, the switcher 600, the real-time processing unit 100, and so forth by outputting the confirmation signal via the second communication port 301*b* connected with the radiation imaging unit 400. The processor 310 may transmit the confirmation signal to at least one of the real-time processing unit 100 and the non-real-time processing unit 200 via both of the first communication port 301*a* and the second communication port 301*b*. At least one of real-time processing unit 100 and the non-real-time processing unit 200 may receive the control signal in both directions.

The processor 310 may determine whether a failure occurs in at least one of the real-time processing unit 100 and the non-real-time processing unit 200 using various methods. The processor 310 may determine whether a failure occurs in at least one of the real-time processing unit 100 and the non-real-time processing unit 200 on the basis of the signal received from the at least one of the real-time processing unit 100 and the non-real-time processing unit 200. For example, the processor 310 may determine whether a failure occurs in at least one of the real-time processing unit 100 and the non-real-time processing unit 200 on the basis of the received response signal 344 (316). The processor 310 may generate a confirmation signal (315), transmit the confirmation signal 348 to at least one of the real-time processing unit 100 and the non-real-time processing unit 200, and determine that a failure has occurred in at least one of the real-time processing unit 100 and the non-real-time processing unit 200 when a predetermined time has elapsed. The processor 310 may determine whether the predetermined time has elapsed using a clock 323. The predetermined time may be determined on the basis of the time in which at least one of the real-time processing unit 100 and the non-real-time processing unit 200 can generate the response signal. The response signal 344 may be transmitted to the processor 310 via at least one of the first communication port 301*a* and the second communication port 302*a*.

The processor 310 may record the occurrence of a failure in the storage unit 320 when it determines that the failure has occurred in at least one of the real-time processing unit 100 and the non-real-time processing unit 200 (317). The storage unit 320 may store data temporarily or non-temporarily. The storage unit 320 may include various kinds of storages and media such as volatile or non-volatile storages such as a ROM 321 or a RAM 322, magnetic disk storages, magnetic tape storages, a CD, or a DVD.

The processor 310 described above may be implemented by one or more semiconductor chips, and the semiconductor chips may be installed in the printed circuit board. The ROM 321, the RAM 322, the magnetic disk storages, or the like, which act as the storage unit 320, may be installed in the printed circuit board.

The switcher 600 may distribute input signals to a plurality of apparatuses. As shown in FIG. 3, the switcher 600 may distribute the input image to a plurality of displays 611 and 612. Each of the displays 611 and 612 may display the distributed image. The switcher 600 may transmit the input images to the corresponding displays 611 and 612 in accordance with the settings. For example, the switcher 600 may transmit the real-time image generated by the real-time processing unit 100 to the first display 611, and the first display 611 may display the real-time image. In addition, the switcher 600 may transmit the non-real-time image generated by the non-real-time processing unit 200 to the second display 612, and the second display 612 may display the non-real-time image.

The console 603 may receive various instructions for controlling general operations of the radiographic imaging apparatus 10. The console 603 may be provided with input devices for receiving instructions according to an operation of the user 98 through various kinds of physical buttons such as a keyboard, a switch button, a touch pad, a touch screen, a trackball, a track pad, an operating stick, or a mouse. In addition, the console 603 may further be provided with a general-purpose serial bus port for inputting data, a CD reader, or a DVD reader. The console 603 may include a display such as monitor for displaying information to the user 98. As shown in FIG. 3, the console 603 may be configured to communicate with the central controller 300 via a wired communication network or a wireless communication network.

The display 610 may display the obtained image or a graphic user interface associated with the radiation imaging control. The radiographic imaging apparatus 10 may include a plurality of displays 611 and 612. Each of the displays 611 and 612 may be set to display the same image. In addition, each of the displays 611 and 612 may be set to display a different image. For example, the first display 611 may be set to display the real-time image generated by the real-time processing unit 100, and the second display 612 may be set to display information associated with the procedure or diagnosis, information associated with operations of the radiographic imaging apparatus 10, the non-real-time image such as a three-dimensional image, information on the subject 99, or various other information in addition to the real-time image. In addition, the displays 611 and 612 may adjoin or each may be provided separately. For example, the first display 611 may be provided inside the imaging room 95, and the second display 612 may be provided outside the imaging room 95. When the displays 611 and 612 are separate from each other, each of the displays 611 and 612 may display the same image. Each of the displays 611 and 612 may be distributed by the switcher 600 to display the received image. The display 610 may be implemented using a plasma display panel (PDP), a light emitting diode (LED), a liquid crystal display (LCD), or a cathode-ray tube (CRT). Additionally, the display 610 may be implemented using various means used for displaying the image.

The subject 99 may include inorganic substances as well as organic substances such as human bodies or animals. A contrast medium may be injected into the subject 99 if necessary. The contrast medium is a chemical that changes the degree to which radiation is absorbed into different tissues to increase the difference of radiation absorption among tissues and enhance the contrast degree of the image. The contrast medium may include an iodine-containing contrast medium, barium sulfate, air, gas, carbonic acid gas, or the like. The user 98 may control the radiographic imaging apparatus 10 to image the subject 99 several times in order to obtain the radiation image of the subject 99 before the contrast medium injection and the radiation image of the subject 99 after the contrast medium injection.

Hereinafter, a procedure for determining occurrence of a failure and causing the non-real-time processing unit 200 to obtain the real-time processing authority according to the occurrence of the failure will be described with reference to FIGS. 14 to 15B.

Figure 14:
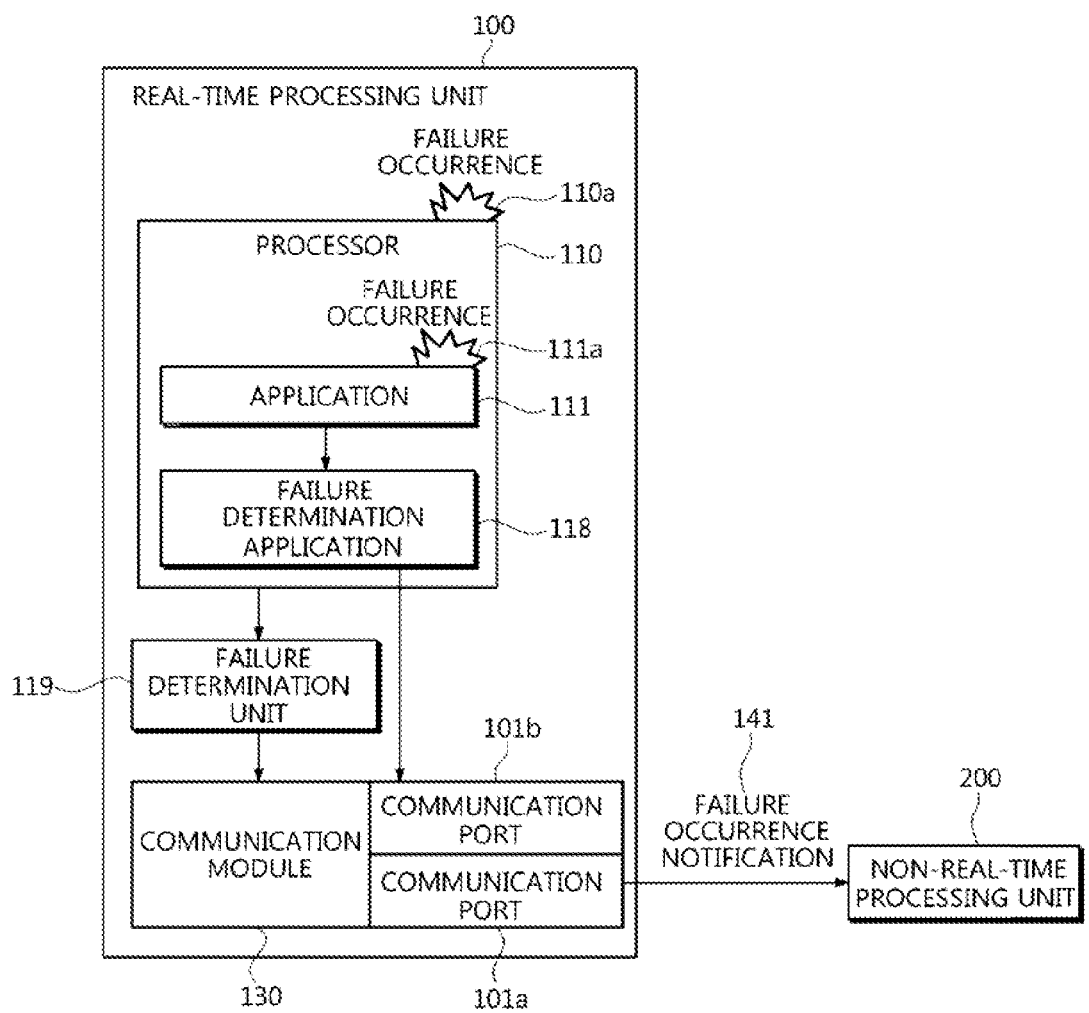
FIG. 14 is a view illustrating an exemplary embodiment of a procedure for determining whether a failure occurs in the real-time processing unit.

FIG. 14 is a view illustrating an exemplary embodiment of the procedure for determining whether a failure occurs in the real-time processing unit. According to an exemplary embodiment, as shown in FIG. 14, the processor 110 may further run the failure determination application 118 and determine whether a failure occurs in the real-time processing application 111 (111a). In this case, the failure may be a failure of the executing real-time processing application 111 itself, a failure of the processor 110, or a failure of another hardware apparatus. The failure may include a software error or crash, a hardware error or crash, a fault, or an event that delays processing such that the real-time processor cannot perform real-time processing. Additionally, the failure may include various kinds of failures that prevent the real-time processing unit 100 from performing the real-time processing. This may be applied to the failure of the real-time processing unit 100 to be described below in the same way. The failure determination application 118 may monitor whether a failure occurs in the real-time processing application 111, and may generate a failure occurrence notification signal 141 for notifying the occurrence of a failure when it determines that a failure has occurred (111a). The failure determination application 118 may transmit a confirmation signal to the real-time processing application 111 and determine whether a failure occurs in accordance with whether the response signal is output from the real-time processing application 111. The failure occurrence notification signal 141 generated by the failure determination application 118 may be transmitted to the non-real-time processing unit 200 via the first communication port 101a of the communication module 130. In some exemplary embodiments, the failure occurrence notification signal 141 may be output via the second communication port 101a and may be transmitted to the non-real-time processing unit 200 via another apparatus. In some exemplary embodiments, the failure determination application 118 may further transmit the real-time processing authority of the real-time processing unit 100 to the non-real-time processing unit 200.

According to an exemplary embodiment, the display 610 may display information indicating that the failure has occurred in the real-time processing unit 100 and/or information indicating the non-real-time processing unit 200 has obtained the real-time processing authority. The display 610 may also display the time the failure occurred and/or the amount of time remaining until the processing of the image is complete. The information may be displayed in the form of an icon, graphic user interface, etc.

According to an exemplary embodiment, as shown in FIG. 14, in addition to the processor 110, the real-time processing unit 100 may be further provided with a failure determination unit 119 for determining a failure. The failure determination unit 119 may include a different and separate application from the processor 110 executing the real-time processing application 111. The failure determination unit 119 may be implemented by a separate apparatus stored in the real-time processing unit 100. The failure determination unit 119 may generate the failure occurrence notification signal 141 for notifying of a failure that occurs in the real-time processing application 111 (111a) or a failure that occurs in the processor 110 itself (110a). The failure occurrence notification signal 141 generated in the same way as described above may be transmitted to the non-real-time processing unit 200 via the first communication port 101a or the second communication port 101b of the communication module 130.

Figure 15A:
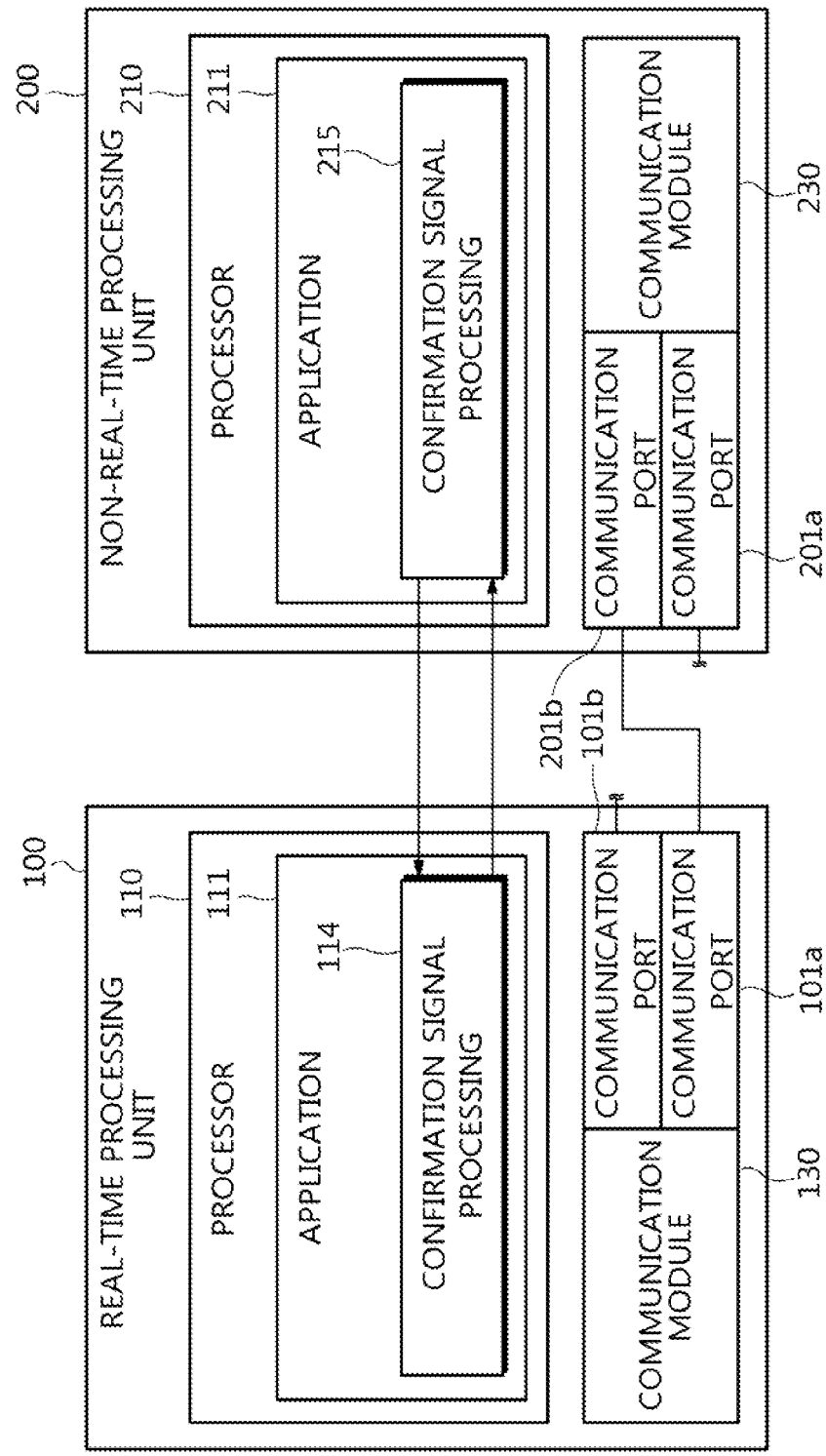
FIGS. 15A and 15B are views illustrating an exemplary embodiment of a procedure for determining whether a failure occurs in the real-time processing unit.
Figure 15B:
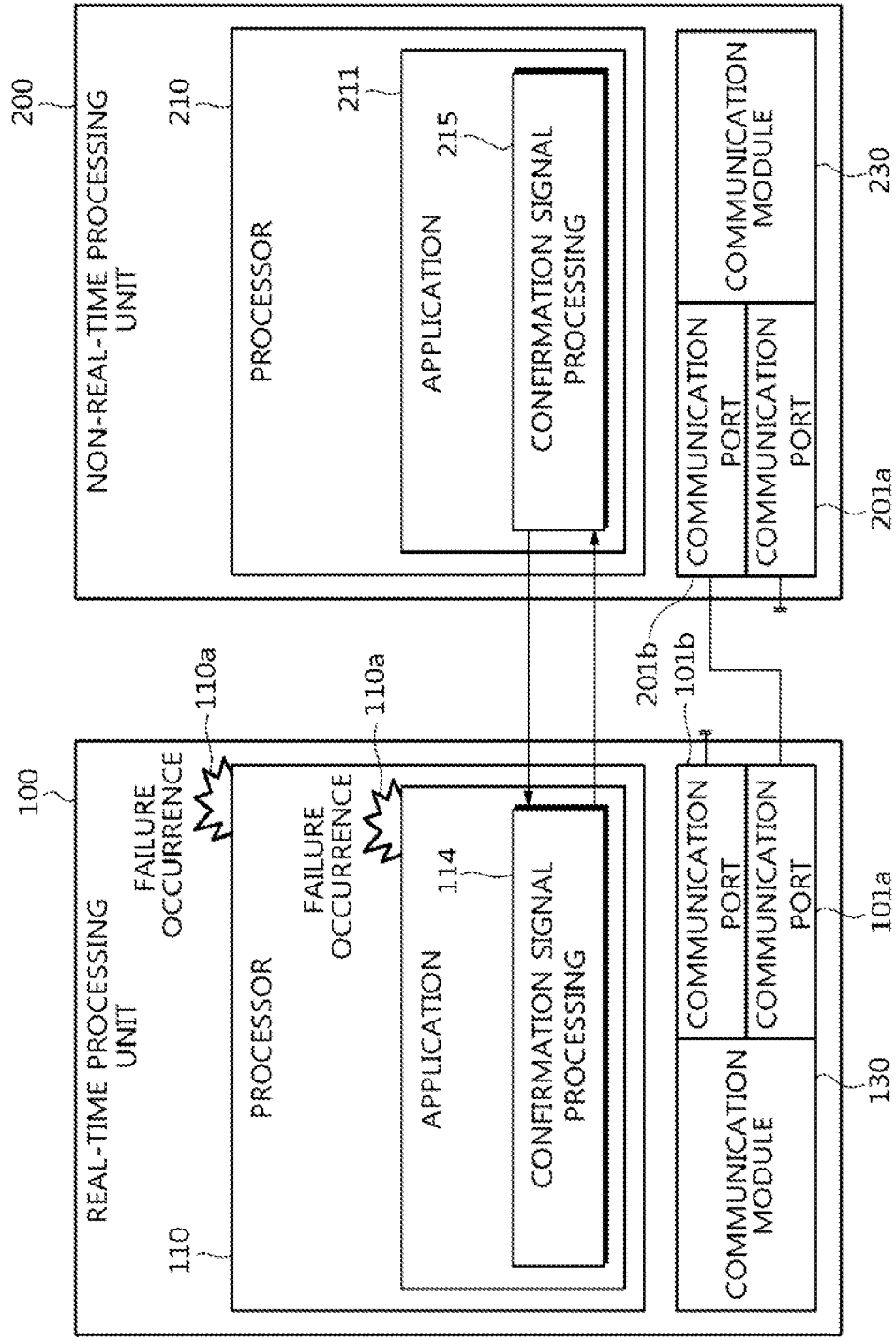

FIGS. 15A and 15B are views illustrating an exemplary embodiment of the procedure for determining whether a failure occurs in the real-time processing unit. Referring to FIG. 15A, the non-real-time processing unit 200 may run the non-real-time application 211, generate a confirmation signal (215), and then transmit the confirmation to the real-time processing unit 100 via the communication ports 101a and 201a of the real-time processing unit 100 and the non-real-time processing unit 200. The real-time processing unit 100 may generate a response signal in accordance with the received confirmation signal (114), and transmit the response signal to the non-real-time processing unit 200 via the communication ports 101a and 201a of the real-time processing unit 100 and the non-real-time processing unit 200. When a failure occurs in the real-time processing unit (110a, 111), the real-time processing unit 100 cannot transmit the response to the confirmation signal to the non-real-time processing unit 200 as shown in FIG. 15B. When the response signal is not received for a predetermined time, the non-real-time processing unit 200 may determine that a failure has occurred in the real-time processing unit 100.

As described above, when a failure occurs in the real-time processing unit 100, the non-real-time processing unit 200 may obtain the real-time processing authority, and perform the real-time image processing that was performed by the real-time processing unit 100 or the real-time control of the radiation imaging unit 400.

Figure 16A:
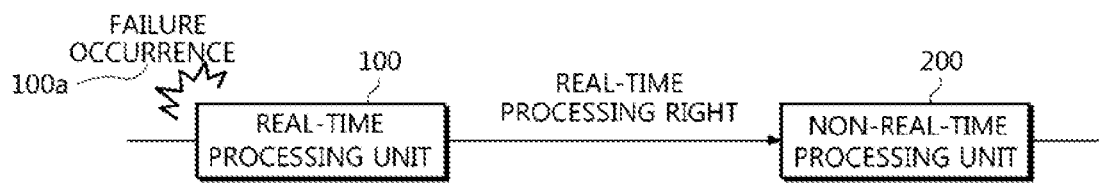
FIGS. 16A and 16B are views illustrating an exemplary embodiment of a procedure in which the non-real-time processing unit obtains a real-time processing authority when a failure occurs in the real-time processing unit.
Figure 16B:
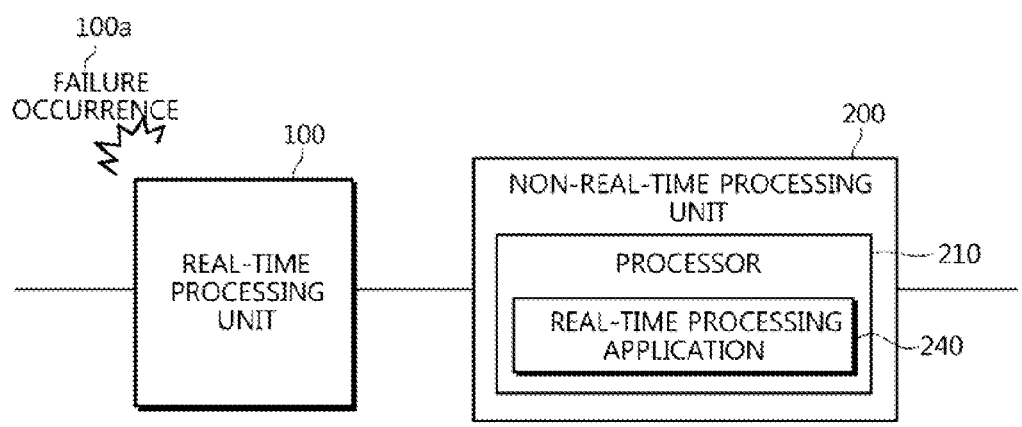

FIGS. 16A and 16B are views illustrating an exemplary embodiment of the procedure in which the non-real-time processing unit obtains the real-time processing authority when a failure occurs in the real-time processing unit. As shown in FIG. 16A, when a failure occurs in the real-time processing unit 100 (100a), the real-time processing unit 100 may transmit the real-time processing authority to the non-real-time processing unit 200. The processor 210 of the non-real-time processing unit 200 may receive the real-time processing authority from the real-time processing unit 100, and run the real-time processing application 240 stored in the storage unit 220 in accordance with the received real-time processing authority. The real-time processing authority may be stored in the storage unit 220 of the non-real-time processing unit 200. Accordingly, the non-real-time processing unit 200 may perform the real-time processing or the real-time control that was performed by the real-time processing unit 100.

Figure 17A:
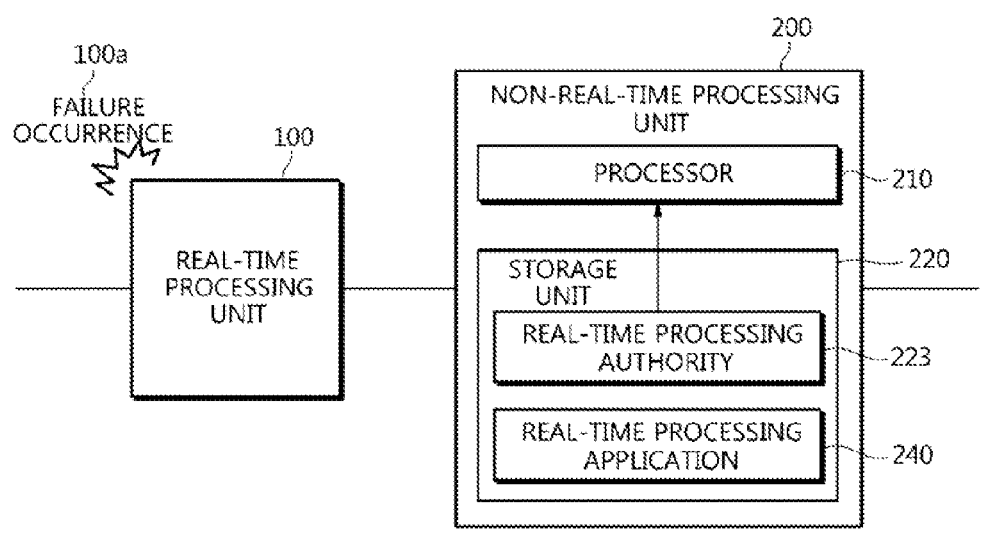
FIGS. 17A and 17B are views illustrating an exemplary embodiment of a procedure in which the non-real-time processing unit obtains the real-time processing authority when a failure occurs in the real-time processing unit.
Figure 17B:
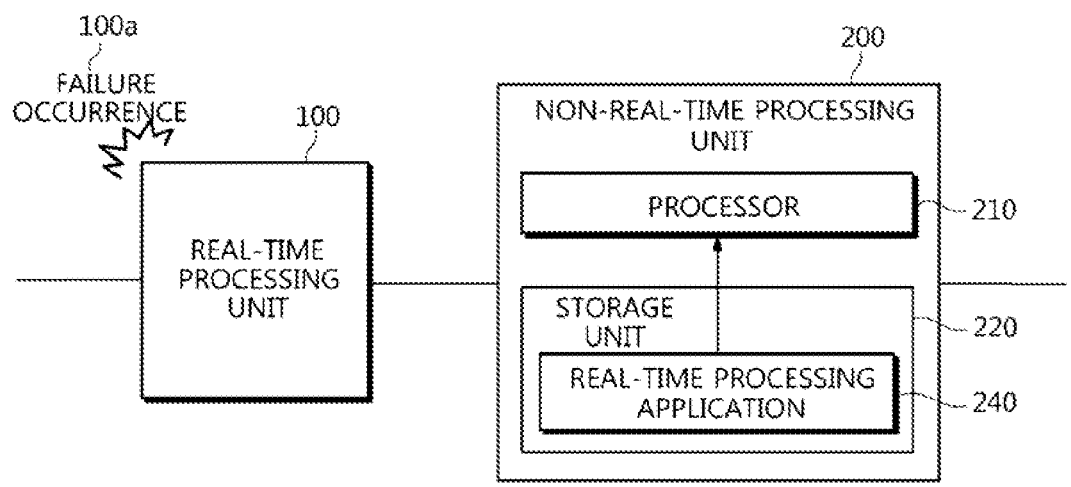

FIGS. 17A and 17B and 16B are views illustrating an exemplary embodiment of the procedure in which the non-real-time processing unit obtains the real-time processing authority when a failure occurs in the real-time processing unit. As shown in FIG. 17A, the non-real-time processing unit 200 may activate the real-time processing authority 223 stored in the storage unit 220 when a failure occurs in the real-time processing unit 100 (100a). In this case, the non-real-time processing unit 20 may determine whether a failure has occurred in the real-time processing unit 100 in accordance with the failure occurrence notification signal transmitted from the real-time processing unit 100 as described above. Alternatively, the non-real-time processing unit 200 may determine that a failure has occurred in the real-time processing unit 100 when the response signal corresponding to the confirmation signal is not transmitted from the real-time processing unit 100 for a predetermined time. When the real-time processing authority 223 is activated, the processor 210 of the non-real-time processing unit 200 may run the real-time processing application 240 as shown in FIG. 17B. Accordingly, the non-real-time processing unit 200 may perform the real-time processing or the real-time control that was performed by the real-time processing unit 100.

The procedure described so far with reference to FIGS. 14 to 17B may be performed even when the central controller 300 is omitted.

Determining the occurrence of a failure on the real-time processing unit 100 and obtaining the real-time control authority of the non-real-time processing unit 200 may be performed by the central controller 300 or may be performed under control of the central controller 300.

Figure 18:
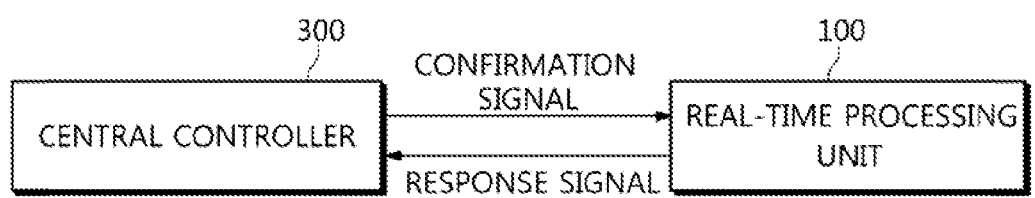
FIG. 18 is a view illustrating an exemplary embodiment of a procedure by which a central controller determines whether a failure occurs in the real-time processing unit when the failure occurs in the real-time processing unit.
Figure 19A:
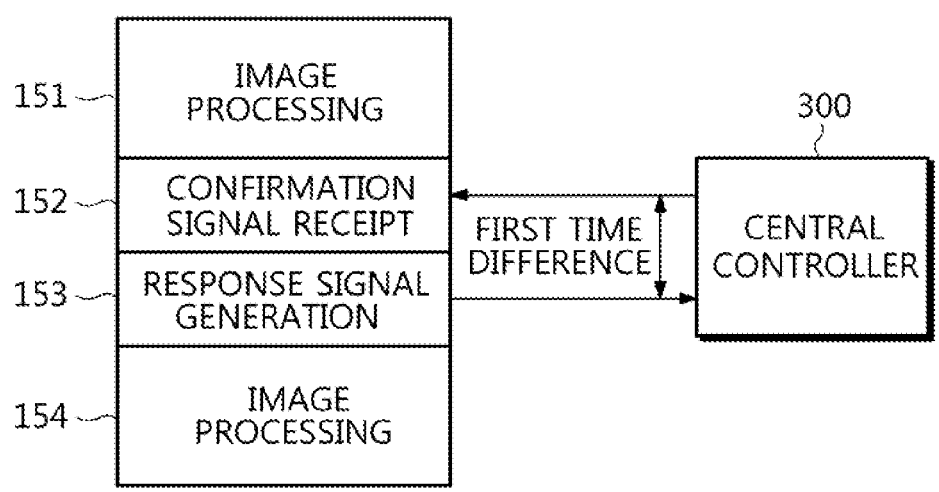
FIGS. 19A and 19B are views illustrating receipt of a confirmation signal and a response signal.
Figure 19B:
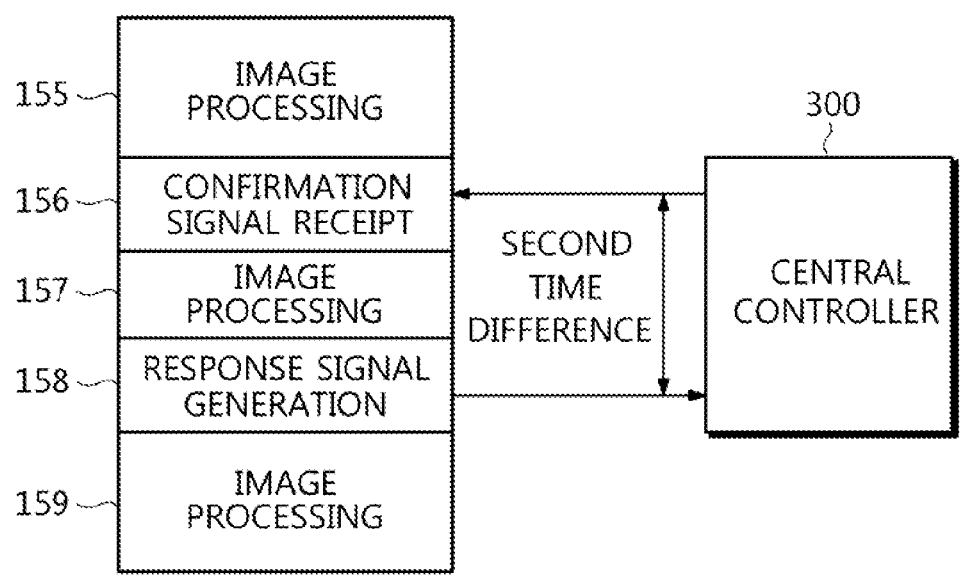

FIG. 18 is a view illustrating an exemplary embodiment of the procedure by which the central controller determines whether a failure occurs in the real-time processing unit when the failure occurs in the real-time processing unit, and FIGS. 19A and 19B are views illustrating receipt of the confirmation signal and the response signal. The central controller 300 may determine whether a failure occurs in the real-time processing unit 100 using the confirmation signal and the response signal. The central controller 300 may generate the confirmation signal in a constant period or in an arbitrary way to transmit the confirmation signal to the real-time processing unit 100 as shown in FIG. 18. The real-time processing unit 100 may generate the response signal responding to the confirmation signal and then transmit the response signal to the central controller 300.

Referring to FIG. 19A, when the real-time processing unit 100 receives the confirmation signal (152) while performing the real-time image processing (151), the real-time processing unit may immediately generate the response signal while stopping or not stopping the real-time image processing (151) and then transmit the response signal to the central controller 300. The real-time processing unit 100 may continue to perform the real-time image processing (154) after transmitting the response signal (153). Referring to FIG. 19B, when the real-time processing unit 100 receives the confirmation signal (156) while performing the real-time image processing (155), the real-time processing unit may further perform the real-time image processing (157) and generate the response signal after a predetermined time is elapsed (158). The generated response signal 158 may be transmitted to the central controller 300. The real-time processing unit 100 may continue to perform the real-time image processing 159 after transmitting the response signal (158). In this case, a second time difference when the central controller receives the response signal after transmitting the confirmation signal may be longer than a first time difference when the real-time processing unit 100 immediately generates the response signal. Accordingly, when the central controller is set to generate the response signal as shown in FIG. 19B, the central controller 300 may wait a long time to receive the response signal.

When the central controller 300 does not receive the response signal within a proper time, for example, a time equal to or longer than the first time difference or the second time difference, the central controller 300 may determine that a failure has occurred in the real-time processing unit 100.

Figure 20:
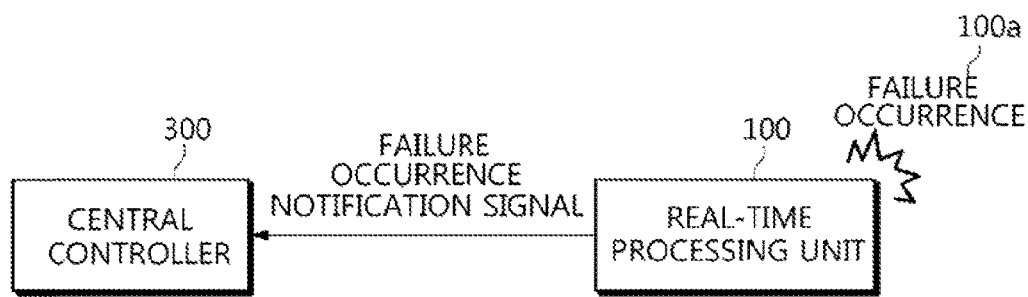
FIG. 20 is a view illustrating an exemplary embodiment of the procedure by which the central controller determines whether a failure occurs in the real-time processing unit when the failure occurs in the real-time processing unit.

FIG. 20 is a view illustrating an exemplary embodiment of the procedure by which the central controller determines whether a failure occurs in the real-time processing unit when the failure occurs in the real-time processing unit. The central controller 300 may determine whether a failure occurs in the real-time processing unit 100 using the failure occurrence notification signal transmitted from the real-time processing unit 100. When a failure occurs (100a), the real-time processing unit 100 may generate the failure occurrence notification signal and then notify the central controller 300 of the occurrence of the failure via the second communication port 101b in the same way as in FIG. 14. The real-time processing unit 100 may also output the failure occurrence notification signal via the second communication port 101a, and the failure occurrence notification signal may be transmitted to the central controller 300 via several apparatuses.

Figure 21A:
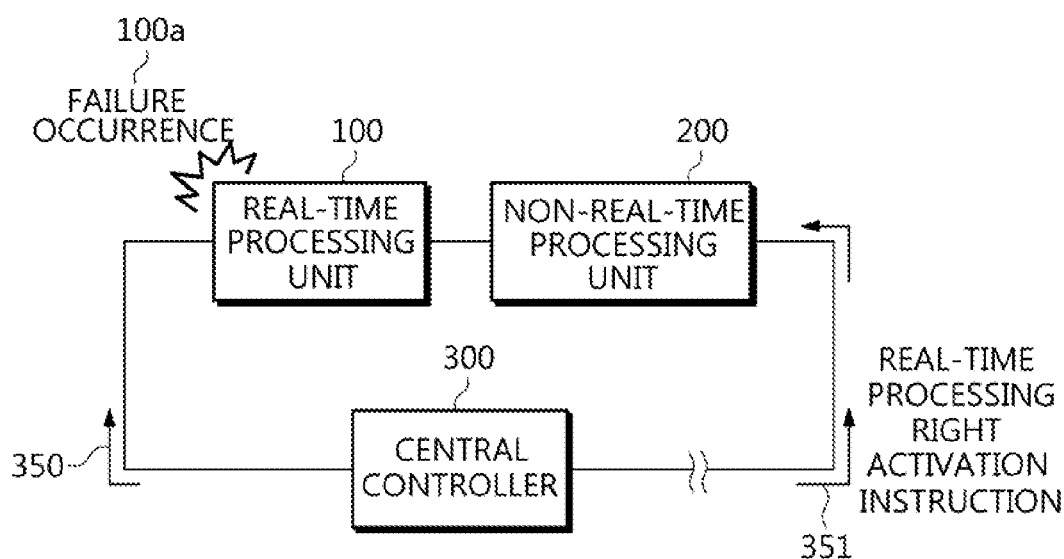
FIGS. 21A and 21B are views illustrating an exemplary embodiment of a procedure in which the central controller causes the non-real-time processing unit to obtain the real-time processing authority when a failure occurs in the real-time processing unit.
Figure 21B:
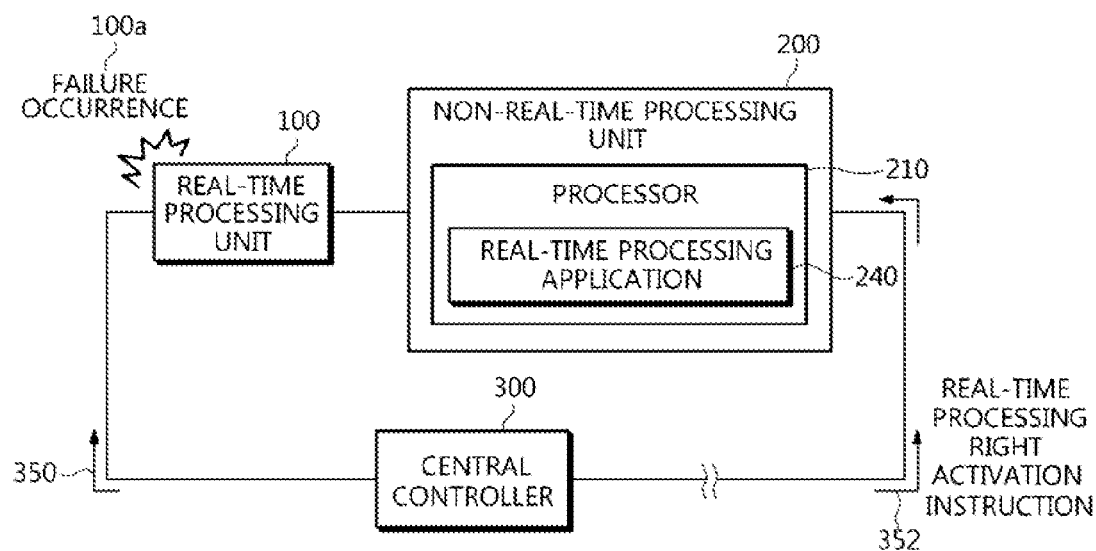

FIGS. 21A and 21B are views illustrating an exemplary embodiment of the procedure in which the central controller causes the non-real-time processing unit to obtain the real-time processing authority when a failure occurs in the real-time processing unit. As shown in FIGS. 21A and 21B, when a failure occurs in the real-time processing unit 100 (100a), the central controller 300 may transmit the real-time processing authority 351 transmitted from the real-time processing unit 100 or stored in the storage unit 320 of the central controller 300 to the non-real-time processing unit 200. When the real-time processing authority 351 is transmitted from the central controller 300, the processor 210 of the non-real-time processing unit 200 may run the real-time processing application 240 stored in the storage unit to perform the real-time processing or the real-time control in accordance with the received real-time processing authority 351. In addition, since the failure has occurred in the real-time processing unit 100 (100a), the real-time processing authority of the central controller 300 is not transmitted via the real-time processing unit 100 but transmitted via another apparatus. The central controller 300 may also be directly connected to the non-real-time processing unit 200 in accordance with the arrangement of the apparatuses. In this case, the real-time processing authority is transmitted to the non-real-time processing unit 200 via no other apparatuses.

Figure 22A:
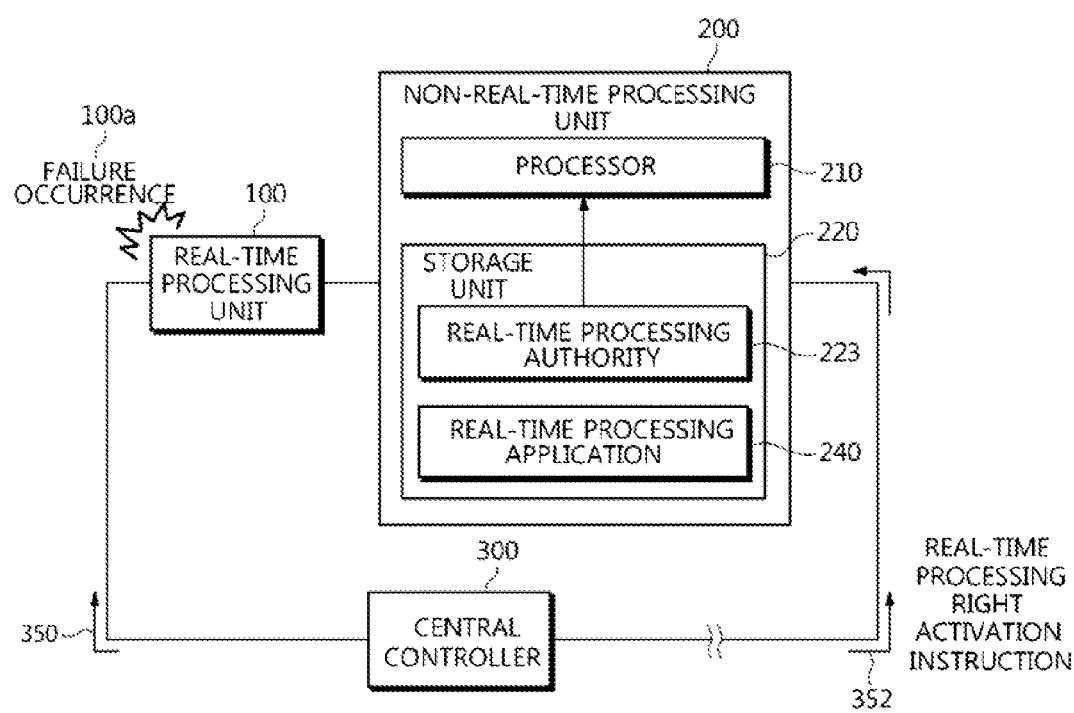
FIGS. 22A and 22B are views illustrating an exemplary embodiment of a procedure in which the central controller causes the non-real-time processing unit to obtain the real-time processing authority when a failure occurs in the real-time processing unit.
Figure 22B:
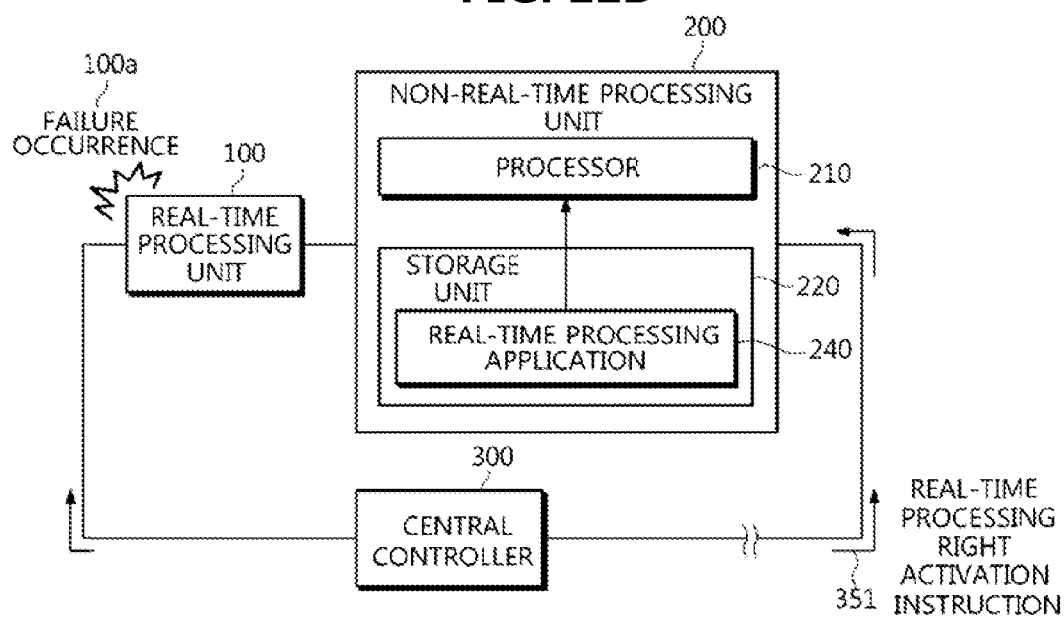

FIGS. 22A and 22B are views illustrating an exemplary embodiment of a procedure in which the central controller causes the non-real-time processing unit to obtain the real-time processing authority when a failure occurs in the real-time processing unit. As shown in FIGS. 22A and 22B, when a failure occurs in the real-time processing unit 100 (100*a*), the central controller 300 may transmit a real-time processing authority activation instruction 352 to the non-real-time processing unit 200, and the non-real-time processing unit 200 may activate the real-time processing authority 223 stored in the storage unit 220 in accordance with the real-time processing authority activation instruction 352. In this case, the real-time processing authority 223 may already be stored in the storage unit 220. When the real-time processing authority 223 is activated, the processor 210 of the non-real-time processing unit 200 may load and run the real-time processing application 240. It is thus possible for the non-real-time processing unit 200 to perform the real-time processing or the real-time control that was performed by the real-time processing unit 100. Since the failure has occurred in the real-time processing unit 100, the real-time processing authority activation instruction 352 of the central controller 300 cannot be transmitted via the real-time processing unit 100 (350) in the same way as described above. Accordingly, the real-time processing authority activation instruction 352 is transmitted directly to the non-real-time processing unit 200 or transmitted to the non-real-time processing unit via other apparatuses in accordance with the arrangement of the apparatuses.

Figure 23:
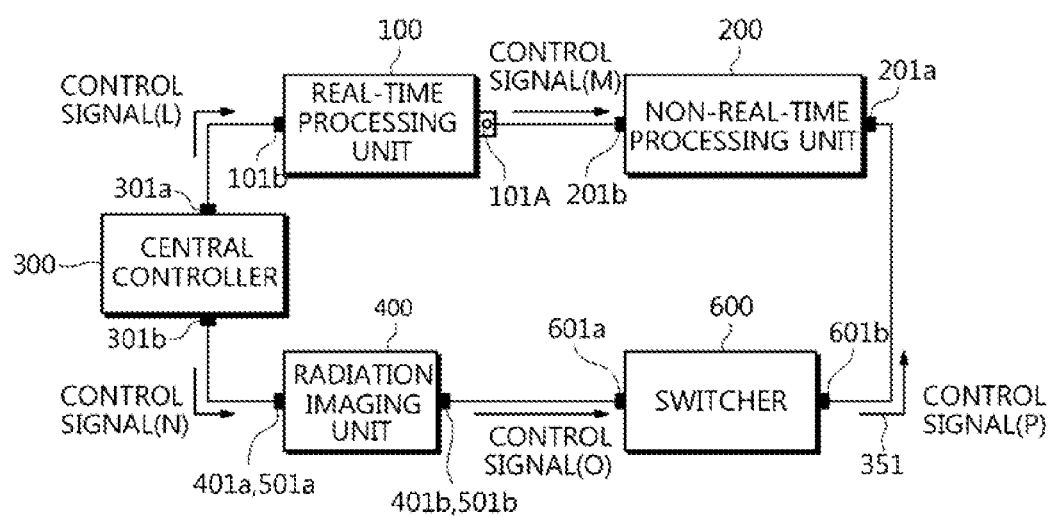
FIGS. 23 and 24 are views illustrating a procedure in which the central controller controls the radiographic imaging apparatus via a ring network.
Figure 24:
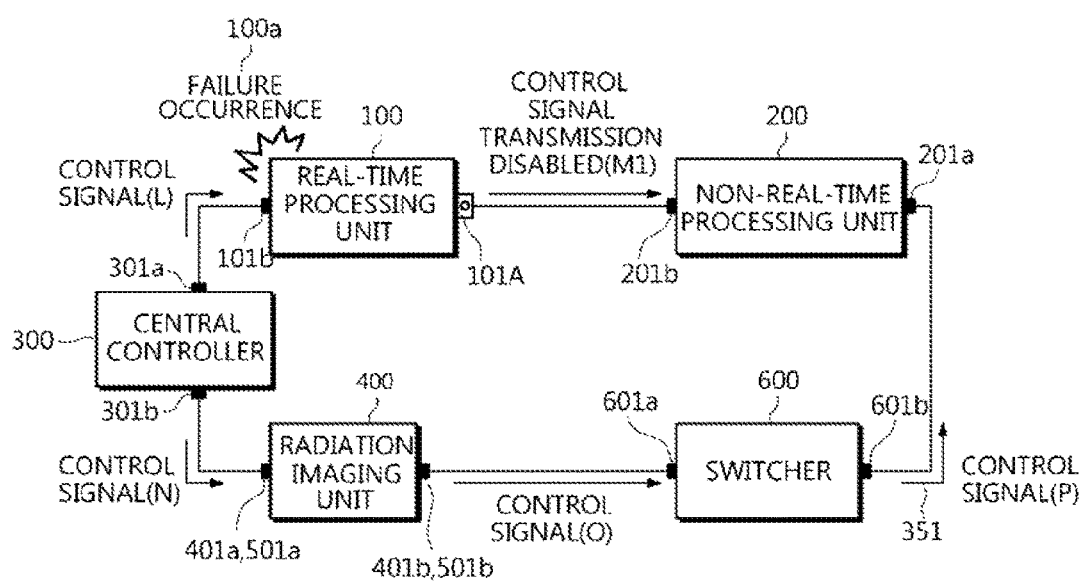

Hereinafter, a procedure in which the central controller controls the radiographic imaging apparatus via a ring network will be described with reference to FIGS. 23 and 24. FIGS. 23 and 24 are views illustrating a procedure in which the central controller controls the radiographic imaging apparatus via the ring network.

Referring to FIG. 23, the first communication port 301*a* of the central controller 300 may be configured to communicate with the second communication port 101*b* of the real-time processing unit 100 via a cable or the like, the first communication port 101*a* of the real-time processing unit 100 may be configured to communicate with the second communication port 201*b* of the non-real-time processing unit 200 via a cable or the like, the first communication port 201*a* of the non-real-time processing unit 200 may be configured to communicate with the second communication port 601*b* of the switcher 600 via a cable or the like, the first communication port 601*a* of the switcher 600 may be configured to communicate with one adaptor 401*b* of the radiation imaging unit 400 via a cable or the like, and another adaptor 401*a* of the radiation imaging unit 400 may be configured to communicate with the second communication port 301*b* of the central controller 300 via a cable or the like. Accordingly, the real-time processing unit 100, the non-real-time processing unit 200, the central controller 300, the radiation imaging unit 400, and the switcher 600 of the radiographic imaging apparatus 10 may be connected in accordance with the ring network.

The central controller 300 may generate a control signal for controlling at least one of the real-time processing unit 100, the non-real-time processing unit 200, the radiation imaging unit 400, and the switcher 600, or generate a confirmation signal for confirming whether a failure occurs in at least one of the real-time processing unit 100 and the non-real-time processing unit 200. The generated control signal or confirmation signal may be transmitted toward the real-time processing unit 100 via the first communication port 301*a* (L) or may be transmitted toward the radiation imaging unit 400 via the second communication port 301*b* (N).

Since the real-time processing unit 100, the non-real-time processing unit 200, the central controller 300, the radiation imaging unit 400, and the switcher 600 are connected by the ring network as described above, the central controller 300 may sequentially transmit the control signal to any one of the real-time processing unit 100, the non-real-time processing unit 200, the switcher 600, and the radiation imaging unit 400 in this connection order. In other words, the central controller 300 may directly transmit the control signal to the radiation imaging unit 400 (N) or may transmit the control signal via the path (L-M-P-O) in the order of the real-time processing unit 100, the non-real-time processing unit 200, the switcher 600, and the radiation imaging unit 400 to finally transmit the control signal to the radiation imaging unit 400. In some exemplary embodiments, the central controller 300 may transmit the control signal to the radiation imaging unit in both directions (L-M-P-O, N). Similarly, the central controller 300 may generally transmit the control signal for the non-real-time processing unit 200, for example, the real-time processing authority activation instruction, via the real-time processing unit 100 (L-M), transmit the control signal via the radiation imaging unit 400 and the switcher 600 (N-O-P), or transmit the control signal via both paths (L-M, N-O-P).

When there is an apparatus in which a failure occurs in the path as shown in FIG. 24 (100*a*), for example, the real-time processing unit 100, transmission via the apparatus in which the failure occurs may be impossible (L-M1). In this case, the central controller 300 may directly transmit the control signal to the radiation imaging unit 400 (M) or transmit the control signal to the non-real-time processing unit 200 via apparatuses 400 and 600 in which no failure occurs (N-O-P). The central controller 300 may determine whether a failure occurs (100*a*) and determine the path through which the control signal is to be transmitted depending on whether a failure occurs (100*a*). In this case, the central controller 300 may determine the path through which the control signal is to be transmitted according to the failure occurrence notification signal transmitted from the real-time processing unit 100 or the non-real-time processing unit 200. In addition, the central controller 300 may determine that a failure has occurred when the response signal is not transmitted from the real-time processing unit 100 or the non-real-time processing unit 200 for a predetermined time and then determine the path through which the control signal is to be transmitted.

In general, the non-real-time processing unit 200 may receive the image data or the control signal via all ports 201*a* and 201*b*, or may transmit the control signal via all ports 201*a* and 201*b*. When a failure occurs in the real-time processing unit 100 (100*a*), the non-real-time processing unit 200 may obtain the real-time processing authority, receive the image data only via another path (O-P) that does not include the real-time processing unit 100, or transmit the control signal for real-time controlling the radiation imaging unit 400 to the radiation imaging unit 400.

Since the real-time processing unit 100, the non-real-time processing unit 200, the central controller 300, the radiation imaging unit 400, and the switcher 600 are connected in accordance with the ring network as described above, each apparatus may be controlled even when failures occur in some of the apparatuses.

Hereinafter, a method of controlling a radiographic imaging apparatus will be described with reference to FIGS. 25 to 28. The method of controlling the radiographic imaging apparatus shown in FIGS. 25 to 28 relates to a method of controlling the radiographic imaging apparatus 10 including the real-time processing unit 100, the non-real-time processing unit 200, the central controller 300, the radiation imaging unit 400, the switcher 600, and so forth. In this case, the central controller 300 and the switcher 600 may be omitted in some exemplary embodiments. When the central controller 300 is omitted, the real-time processing unit 100 or the non-real-time processing unit 200 may separately control the radiation imaging unit 400, and the real-time processing unit 100 and the non-real-time processing unit 200 may control the radiation imaging unit 400 in connection with each other in some exemplary embodiments. The radiation imaging unit 400 may further include adaptors 412, 432, 434, 491, and 493 if necessary. The adaptors 412, 432, 434, 491, and 493 may act to cause the respective operating units 411, 431, 440, 490, and 493 of the radiation imaging unit 400 having an existing-type interface to be connected to a network implementing a high performance serial fieldbus. The real-time processing unit 100, the non-real-time processing unit 200, the central controller 300, the radiation imaging unit 400, the switcher 600, and so forth may be connected by the ring network.

Figure 25:
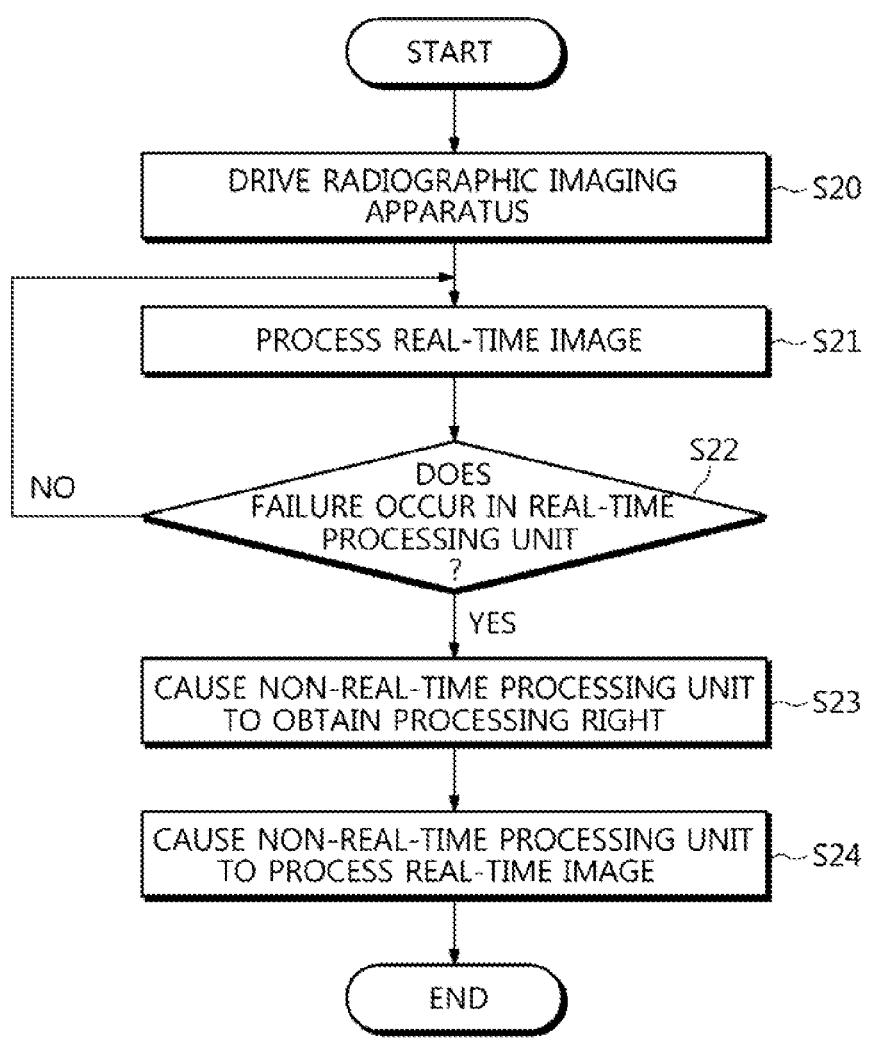
FIG. 25 is a flow chart illustrating an exemplary embodiment of a method of controlling the radiographic imaging apparatus.

FIG. 25 is a flow chart illustrating an exemplary embodiment of a method of controlling the radiographic imaging apparatus.

According to the method of controlling the radiographic imaging apparatus shown in FIG. 25, first, the radiographic imaging apparatus 10 may start operating by means of the user's operations or predefined settings. The real-time processing unit 100, the non-real-time processing unit 200, the central controller 300, the radiation imaging unit 400, and so forth of the radiographic imaging apparatus 10 may be individually booted (operation s20). When the booting is finished, the real-time processing unit 100, the non-real-time processing unit 200, the central controller 300, the radiation imaging unit 400, and so forth perform prearranged operations.

When the radiographic imaging apparatus 10 starts operating, the radiation imaging unit 400 may apply the radiation to the subject 99 to obtain image data that is raw data with respect to the subject 99, and the real-time processing unit 100 may use the image data to perform the real-time image processing (operation s21). In this case, the real-time image processing may include generation of the real-time radiation image, real-time correction of the radiation image, the DSA processing, and so forth. The real-time image processing may be performed in connection with obtaining the image data.

The non-real-time processing unit 200 may use the image data to perform the non-real-time image processing. In this case, the non-real-time image processing may include generation of the non-real-time radiation image, non-real-time correction of the radiation image, generation of the stereoscopic radiation image, generation of the three-dimensional stereoscopic image, the volume data processing, or the like. The central controller 400 may control general operations of the real-time processing unit 100, the non-real-time processing unit 200, the radiation imaging unit 400, the switcher 600, and so forth. In some exemplary embodiments, the real-time operation of the radiation imaging unit 400 may be controlled by the real-time processing unit 100.

When a failure occurs in the real-time processing unit 100 (operation s22), the non-real-time processing unit 200 may obtain the real-time processing authority (operation s23), and perform the real-time processing including the real-time image processing or the real-time control that was performed by the real-time processing unit 100 in accordance with the obtained real-time processing authority (operation s24). Whether a failure occurs in the real-time processing unit 100 (operation s22) may be determined by the non-real-time processing unit 200 or the central controller 400. In this case, the failure may include not only a failure of the executing real-time processing application 111 but also a failure of the processor 110 itself. Obtaining the real-time processing authority may be performed by the non-real-time processing unit 200, and the non-real-time processing unit 200 may be controlled by the central controller 400. While the non-real-time processing unit 200 performs the real-time image processing or the real-time control in accordance with the real-time processing authority (operation s24), the real-time processing unit 100 may be automatically or manually restored. For example, the real-time processing unit 100 may be rebooted while the non-real-time processing unit 200 performs the real-time processing, may repair the failure by executing an operating system (OS) in a restoring mode, or may be initialized. When the failure of the real-time processing unit 100 is resolved, the real-time processing unit 100 may obtain the real-time processing authority again and the non-real-time processing unit 200 may lose the real-time processing authority. Accordingly, the real-time processing unit 100 may resume performing the real-time processing and the non-real-time processing unit 200 may only perform the non-real-time processing. In this case, when the failure is resolved, the real-time processing unit 100 may transmit a signal associated with resolution of the failure to the non-real-time processing unit 200 to cause the non-real-time processing unit 200 to lose the real-time processing authority.

Hereinafter, several exemplary embodiments of the method of controlling the radiographic imaging apparatus will be described in more detail.

Figure 26:
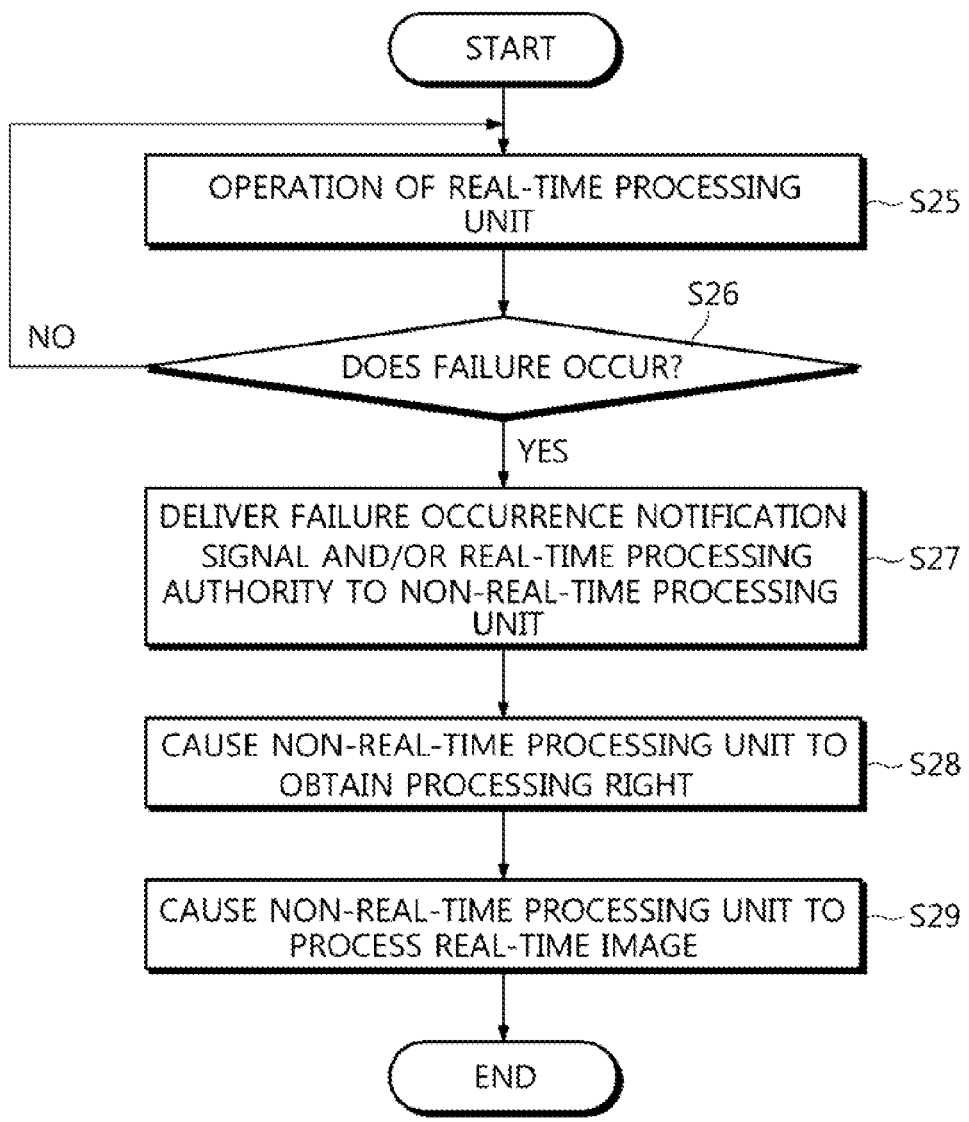
FIG. 26 is a flow chart illustrating an exemplary embodiment of the method of controlling the radiographic imaging apparatus.

FIG. 26 is a flow chart illustrating an exemplary embodiment of the method of controlling the radiographic imaging apparatus.

Referring to FIG. 26, the radiographic imaging apparatus 10 may start operating by means of the user's operation or predefined settings and the real-time processing unit 100 may thus perform the real-time processing (operation s25).

When a failure occurs in the real-time processing unit 100 while the real-time processing is performed (operation s26), the real-time processing unit 100 may directly sense the occurrence of the failure and transmit the failure occurrence notification signal to the non-real-time processing unit 200, transmit the real-time processing authority to the non-real-time processing unit, or transmit both of the failure occurrence notification signal and the real-time processing authority to the non-real-time processing unit (operation s27). In this case, the failure may include not only a failure occurring while the real-time processing application 111 is being executed, but also a failure of the processor 110 itself. According to an exemplary embodiment, the real-time processing unit 100 may use the real-time processing application 111 and a separate failure determination application 118 to determine whether a failure has occurred while the real-time processing application 111 is executing. According to an exemplary embodiment, the real-time processing unit 100 may determine whether a failure occurs in the processor 110, the real-time processing application 111, or other hardware using the separate failure determination unit 119.

The non-real-time processing unit 200 may obtain the real-time processing authority in accordance with the signal transmitted from the real-time processing unit 100 (operation s28). According to an exemplary embodiment, when the non-real-time processing unit 200 receives the failure occurrence signal, the non-real-time processing unit may activate the real-time processing authority already stored in the storage unit 220 of the non-real-time processing unit 200 to obtain the real-time processing authority in accordance with the failure occurrence signal. According to an exemplary embodiment, the non-real-time processing unit 200 may receive the real-time processing authority from the real-time processing unit 100 to obtain the real-time processing authority.

Although not shown in the drawings, the non-real-time processing unit 200 may transmit the confirmation signal to the real-time processing unit 100 and then determine whether a failure occurs in the real-time processing unit 100 in accordance with whether the response signal corresponding to the confirmation signal is transmitted from the real-time processing unit 100 in some exemplary embodiments. When the response signal is not received, the non-real-time processing unit 200 may determine that a failure has occurred in the real-time processing unit 100 and activate the already stored real-time processing authority to obtain the real-time processing authority.

When the non-real-time processing unit 200 obtains the real-time processing authority, the non-real-time processing unit may perform the real-time processing such as the real-time image processing or the real-time control of the radiation imaging unit 400 in accordance with the obtained real-time processing authority (operation s29) instead of the real-time processing unit 100. The real-time processing unit 100 may resolve the failure and may be restored while the non-real-time processing unit 200 performs the real-time processing. When the failure of the real-time processing unit 100 is resolved, the real-time processing unit 100 may obtain the real-time processing authority again to perform the real-time processing, and the non-real-time processing unit 200 may lose the real-time processing authority so that the non-real-time processing unit 200 cannot perform the real-time processing. The non-real-time processing unit 200 may determine whether the real-time processing unit 100 is completely restored in accordance with the failure occurrence signal or the response signal corresponding to the confirmation signal transmitted from the real-time processing unit 100, and may discard and lose the real-time processing authority when it determines that the real-time processing unit 100 is completely restored.

Figure 27:
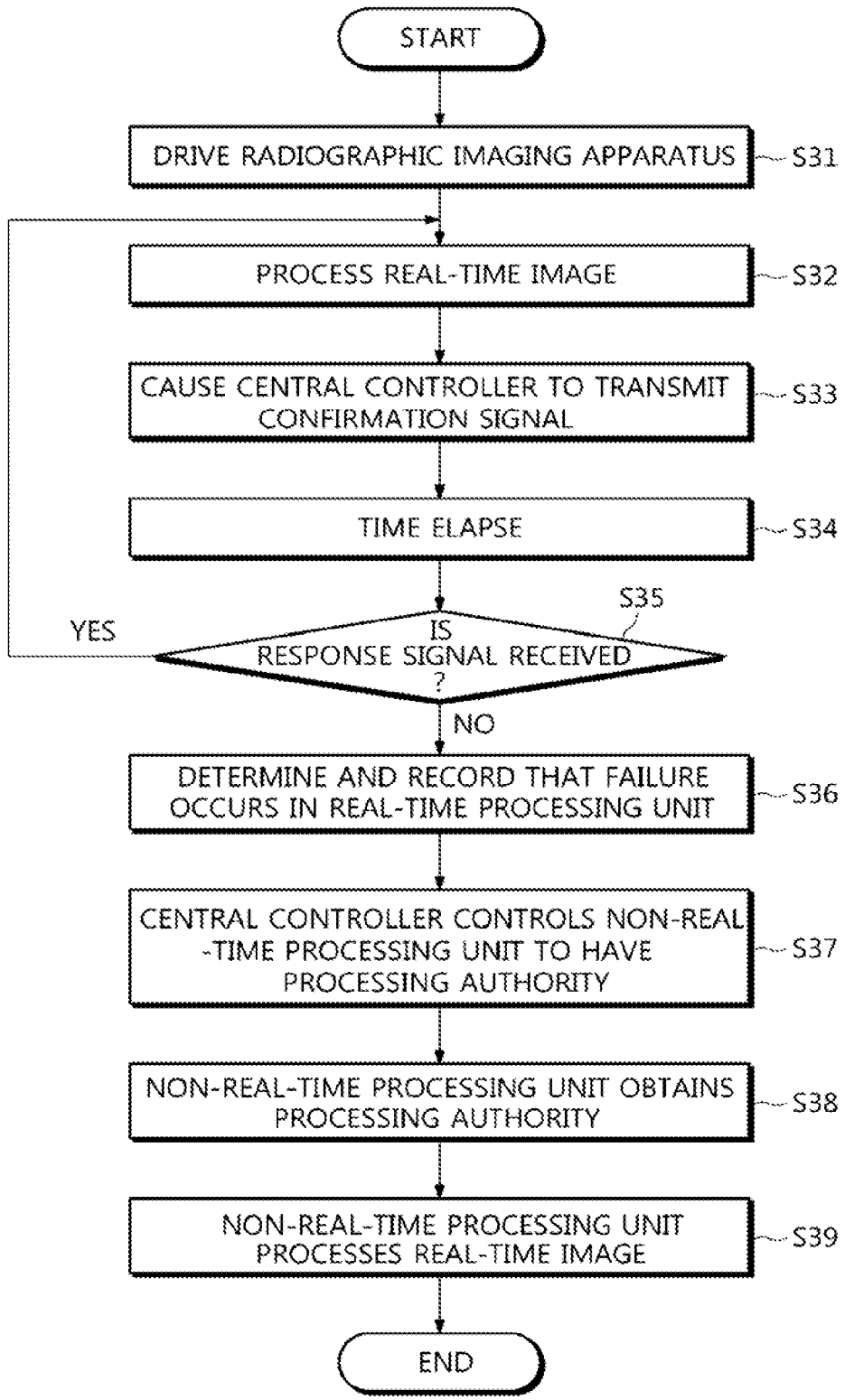
FIG. 27 is a flow chart illustrating an exemplary embodiment of the method of controlling the radiographic imaging apparatus.

FIG. 27 is a flow chart illustrating an exemplary embodiment of the method of controlling the radiographic imaging apparatus.

Referring to FIG. 27, the real-time processing unit 100 and the non-real-time processing unit 200 may perform the real-time processing under control of the central controller 300.

First, when the radiographic imaging apparatus 10 starts operating in accordance with the user's operation or predefined settings, the real-time processing unit 100, the non-real-time processing unit 200, the central controller 300, the radiation imaging unit, and so forth of the radiographic imaging apparatus 10 may be individually booted (operation s31).

When the radiation imaging unit 400 performs the radiation imaging to obtain the image data, the real-time processing unit 100 may use the image data to generate the real-time image or perform the associated real-time image processing (operation s31). In an exemplary embodiment, the real-time processing unit 100 may control real-time operations of the radiation imaging unit 400.

While the real-time processing unit 100 performs the real-time image processing (operation s31), the central controller 400 may transmit the confirmation signal to the real-time processing unit 100 (operation s33). The confirmation signal may be transmitted via the ring network in the form of a datagram. Transmission of the confirmation signal may be immediately initiated when booting of the central controller 300 is finished. Generation and transmission of the confirmation signal may be performed periodically at preset timings or intervals or aperiodically.

When the central controller receives the response signal (operation s34) before a predefined time has elapsed (operation s34), the central controller 400 may determine that the real-time processing unit 100 does not operate normally. When the central controller does not receive the response signal (operation s35—NO) even after the predefined time has elapsed (operation s33), the central controller 400 may determine that a failure has occurred in the real-time processing unit 100 (operation s36). In addition, the central controller 400 may record associated content in the failure occurrence history when it determines that a failure has occurred in the real-time processing unit 100. In this case, the failure may include not only a failure of the real-time processing application 111 run in the real-time processing unit 100 but also a failure of the processor 110 of the real-time processing unit 100 itself.

The central controller 400 may control the non-real-time processing unit such that the non-real-time processing unit 200 has the real-time processing authority (operation s37). According to an exemplary embodiment, the central controller 400 may transmit data associated with the real-time processing authority to the non-real-time processing unit 200. According to an exemplary embodiment, the central controller 400 may transmit the real-time processing authority activation instruction to the non-real-time processing unit 200. The central controller 400 may continue to transmit the confirmation signal to the real-time processing unit 100 to determine whether the real-time processing unit 100 has been restored from the failure even after the non-real-time processing unit 200 has the real-time processing authority.

The non-real-time processing unit 200 may obtain the real-time processing authority (operation s38). According to an exemplary embodiment, the non-real-time processing unit 200 may obtain the real-time processing authority by means of the data associated with the real-time processing authority transmitted by the central controller 400. According to an exemplary embodiment, when the non-real-time processing unit receives the real-time processing authority activation instruction, the non-real-time processing unit 200 may activate the real-time processing authority stored in the storage unit 220 to obtain the real-time processing authority.

When the non-real-time processing unit obtains the real-time processing authority, the non-real-time processing unit 200 may perform the real-time processing such as the real-time image processing or the real-time control of the radiation imaging unit 400 in accordance with the obtained real-time processing authority (operation s39) instead of the real-time processing unit 200. The real-time processing unit 100 may fix the failure and be restored while the non-real-time processing unit 200 performs the real-time processing.

When the failure of the real-time processing unit 100 is resolved, the real-time processing unit 100 may obtain the real-time processing authority again to perform the real-time processing. When the central controller receives, again from the real-time processing unit 100, the response signal corresponding to the confirmation signal transmitted to the real-time processing unit 100, the central controller 300 may determine that the failure of the real-time processing unit 100 is resolved. In some exemplary embodiments, the central controller 300 may receive, from the real-time processing unit 100, a restoring completion signal including the content that the real-time processing unit 100 is restored from the failure, and determine that the failure of the real-time processing unit 100 is resolved in accordance with the received restoring completion signal.

Figure 28:
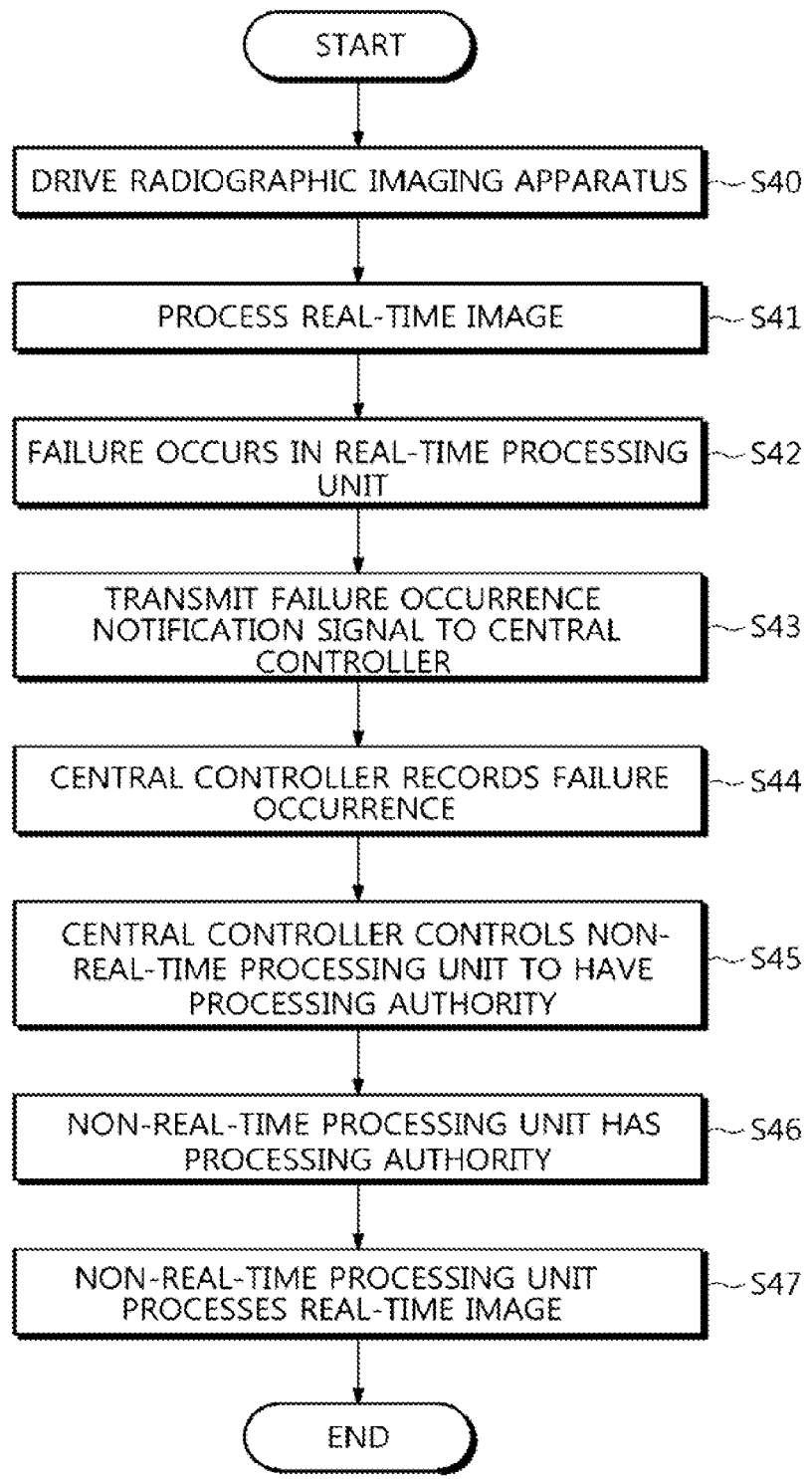
FIG. 28 is a flow chart illustrating an exemplary embodiment of the method of controlling the radiographic imaging apparatus.

FIG. 28 is a flow chart illustrating an exemplary embodiment of the method of controlling the radiographic imaging apparatus.

Referring to FIG. 28, the radiographic imaging apparatus 10 may first start operating by means of the user's operations or predefined settings, and the real-time processing unit 100, the non-real-time processing unit 200, the central controller 300, the radiation imaging unit 400, and so forth of the radiographic imaging apparatus 10 may be individually booted and activated (operation s40).

The radiation imaging unit 400 may obtain image data of the subject 99, and the real-time processing unit 100 may use the image data to generate the real-time image or perform the associated real-time image processing (operation s41). In some exemplary embodiments, the real-time processing unit 100 may control real-time operations of the radiation imaging unit 400.

When a failure occurs while the real-time processing unit performs the real-time processing, the real-time processing unit 100 may use the failure determination application 118 or the failure determination unit 119 to transmit the failure occurrence notification signal to the central controller 300 (operation s43). In this case, the failure may include not only a failure of the executing real-time processing application 111 but also a failure of the processor 110 itself.

When the central controller receives the failure occurrence notification signal, the central controller 300 may determine that a failure has occurred in the real-time processing unit 100 and record the occurrence of the failure in the log (operation s44).

At the same time or at different times, the central controller 300 and the central controller 400 may control the non-real-time processing unit 200 to have the real-time processing authority (operation s45), and the non-real-time processing unit 200 may obtain the real-time processing authority under control of the central controller 400 (operation s46). In this case, the central controller 400 may transmit data associated with the real-time processing authority to the non-real-time processing unit 200, and the non-real-time processing unit 200 may obtain the real-time processing authority by means of the data associated with the real-time processing authority transmitted by the central controller 400. In addition, the central controller 400 may transmit the real-time processing authority activation instruction to the non-real-time processing unit 200, and the non-real-time processing unit 200 may activate the real-time processing authority already stored in the storage unit 220 in accordance with the real-time processing authority activation instruction, thereby obtaining the real-time processing authority.

When the non-real-time processing unit 200 obtains the real-time processing authority, the non-real-time processing unit 200 may perform the real-time processing such as the real-time image processing or the real-time control of the radiation imaging unit 400 in accordance with the obtained real-time processing authority instead of the real-time processing unit 100 (operation s47). While the non-real-time processing unit 200 performs the real-time processing, the real-time processing unit 100 may fix the failure and be restored. The real-time processing unit 100 may transmit the restoring completion signal to the central controller 300 when the real-time processing unit is restored from the failure, and the central controller 300 may control the real-time processing unit 100 to obtain the real-time processing authority again in accordance with the restoring completion signal.

The method of controlling the radiographic imaging apparatus as described above may be applied in the same way or with slight modifications even when a failure occurs not in the real-time processing unit 100 but in the non-real-time processing unit 200. In this case, the real-time processing unit 100 may perform non-real-time processing functions of the non-real-time processing unit 200.

Although a few exemplary embodiments have been shown and described, it would be appreciated by those skilled in the art that changes may be made in these exemplary embodiments without departing from the principles and spirit of the inventive concept, the scope of which is defined in the claims and their equivalents.

What is claimed is:

1. A radiographic imaging apparatus for processing medical images, comprising:
    an imager configured to obtain image data of a subject;
    a real-time processor configured to communicate with the imager and configured to obtain real-time processing authority and perform real-time image processing on the image data; and
    a non-real-time processor configured to communicate with the imager and configured to perform non-real-time image processing on the image data,
    wherein the non-real-time processor is further configured to obtain the real-time processing authority and perform the real-time image processing on the image data in response to a failure occurring in the real-time processor.

2. The radiographic imaging apparatus according to claim 1, wherein the real-time processor is further configured to transmit the real-time processing authority of the real-time processor to the non-real-time processor so that the non-real-time processor obtains the real-time processing authority in response to a failure occurring in the real-time processor.

3. The radiographic imaging apparatus according to claim 1, wherein the non-real-time processor is further configured to determine whether a failure occurs in the real-time processor based on whether the non-real-time processor receives a signal transmitted from the real-time processor or content of the signal.

4. The radiographic imaging apparatus according to claim 3, wherein the real-time processor is further configured to notify the non-real-time processor of an occurrence of a failure in response to the failure occurring in the real-time processor.

5. The radiographic imaging apparatus according to claim 1, further comprising:
    a central controller configured to control operations of the imager, the real-time processor, and the non-real-time processor, and further configured to detect whether a failure occurs in the real-time processor or the non-real-time processor.

6. The radiographic imaging apparatus according to claim 5, wherein the central controller is further configured to detect whether a failure occurs in the real-time processor or the non-real-time processor based on a signal received from the real-time processor or the non-real-time processor.

7. The radiographic imaging apparatus according to claim 5, wherein the central controller transmits a confirmation signal to the real-time processor or the non-real-time processor, the real-time processor or the non-real-time processor transmits a response signal with respect to the confirmation signal to the central controller, and the central controller determines whether a failure occurs in the real-time processor or the non-real-time processor in accordance with the response signal.

8. The radiographic imaging apparatus according to claim 7, wherein the real-time processor is further configured to generate the response signal to the confirmation signal and transmit the response signal to the central controller while processing the image in real time.

9. The radiographic imaging apparatus according to claim 5, wherein the central controller is further configured to control the non-real-time processor to obtain the real-time processing authority in response to a failure occurring in the real-time processor.

10. The radiographic imaging apparatus according to claim 5, wherein the imager, the real-time processor, the non-real-time processor, and the central controller are configured to communicate with each other via a ring network.

11. The radiographic imaging apparatus according to claim 5, wherein the central controller is further configured to determine a control path in accordance with an occurrence of the failure, in response to a failure occurring in at least one of the imager, the real-time processor, and the non-real-time processor.

12. The radiographic imaging apparatus according to claim 10, wherein the central controller is further configured to transmit a control signal to the non-real-time processor along a path that does not include the real-time processor in response to a failure occurring in the real-time processor.

13. The radiographic imaging apparatus according to claim 1, wherein the imager, the real-time processor, and the non-real-time processor are configured to communicate with each other via a ring network.

14. The radiographic imaging apparatus according to claim 1, wherein the imager comprises an adaptor connecting an operating device having a non-standard interface to a network transmitting data in accordance with a predefined standard.

15. The radiographic imaging apparatus according to claim 14, wherein the operating device comprises at least one of a radiation applier configured to generate radiation to be applied to the subject and apply the radiation in the subject direction, a collimator configured to filter the radiation generated in the radiation applier, an anti-scatter grid configured to filter the radiation that has passed through the subject, and a radiation detector configured to receive the radiation that has passed through the subject and obtain the image data.

16. The radiographic imaging apparatus according to claim 1, wherein the real-time processor is further configured to transmit one or more real-time images and associated data obtained by the real-time image processing to the non-real-time processor while performing the real-time image processing.

17. The radiographic imaging apparatus according to claim 1, wherein the non-real-time processor executes the same application as the application for the real-time control of the real-time processor in response to the non-real-time processor obtaining a control authority regarding real-time control of the imager.

18. The radiographic imaging apparatus according to claim 1, wherein the non-real-time image processing comprises at least one of generation of a real-time radiation image and digital subtraction angiography (DSA) processing.

19. A medical imaging apparatus comprising:
an imager configured to image a subject to obtain image data;
a real-time processor configured to control a real-time operation of the imager in accordance with a control authority regarding real-time control of the imager; and
a non-real-time processor configured to perform non-real-time processing of the imager,
wherein the non-real-time processor obtains the control authority regarding real-time control of the imager and controls the real-time operation of the imager in accordance with the control authority, in response to a failure occurring in the real-time processor.

20. A method of controlling a radiographic imaging apparatus including an imager configured to obtain image data, a real-time processor configured to perform real-time image processing on the image data, and a non-real-time processor configured to perform non-real-time image processing on the image data, the method comprising:
obtaining, by the imager, the image data;
performing, by the real-time processor, the real-time image processing on the image data in accordance with a real-time processing authority;
obtaining, by the non-real-time processor, the real-time processing authority of the image data in response to a failure occurring in the real-time processor; and
performing, by the non-real-time processor, the real-time image processing on the image data.

21. The method according to claim 20, further comprising:
transmitting, by the real-time processor, the real-time processing authority of the real-time processor to the non-real-time processor in response to a failure occurring in the real-time processor.

22. The method according to claim 20, wherein the obtaining, by the non-real-time processor, the real-time processing authority of the image data in response to a failure occurring in the real-time processor further comprises determining whether a failure occurs in the real-time processor based on whether a signal transmitted from the real-time processor or content of the signal is received.

23. The method according to claim 20, wherein the radiographic imaging apparatus further comprises a central controller, the method further comprising:
transmitting, by a central controller, a confirmation signal to the real-time processor or the non-real-time processor;
transmitting, by the real-time processor or the non-real-time processor, a response signal to the confirmation signal to the central controller; and
detecting, by the central controller, whether a failure occurs in the real-time processor or the non-real-time processor in accordance with the response signal.

24. The method according to claim 23, further comprising:

controlling, by the central controller, the real-time processing authority already stored in the central controller to be transmitted to the non-real-time processor to cause the non-real-time processor to obtain the non-real-time processor.

25. The method according to claim 23, wherein the imager, the real-time processor, the non-real-time processor, and the central controller are configured to communicate with each other via a ring network.

26. The method according to claim 25, wherein the central controller sequentially transmits a control signal to the imager, the real-time processor, and the non-real-time processor in the sequence in which they are connected.

27. The method according to claim 25, wherein the central controller changes a control path in accordance with the occurrence of a failure in response to the failure occurring in at least one of the imager, the real-time processor, and the non-real-time processor.

28. A method of controlling a radiographic imaging apparatus, the method comprising:

imaging a subject, by using the radiographic imagining apparatus, to obtain image data;

performing real-time processing on the image data in accordance with a control authority regarding real-time control of the imaging;

detecting a failure in the performing of the real-time processing;

obtaining, by a non-real-time processor, real-time processing authority in response to the detecting of the failure in the performing of the real-time processing; and performing, by the non-real-time processor, the real-time image processing on the image data.

* * * * *